(12) United States Patent
Chen et al.

(10) Patent No.: US 9,987,237 B2
(45) Date of Patent: **\*Jun. 5, 2018**

(54) METHODS AND DEVICES FOR USING ISOPERILLYL ALCOHOL

(71) Applicant: NEONC TECHNOLOGIES INC., Los Angeles, CA (US)

(72) Inventors: Thomas Chen, La Canada, CA (US); Daniel Levin, La Canada, CA (US); Satish Pupalli, Rancho Cucamonga, CA (US); Daniel Anthony Dickman, San Ramon, CA (US)

(73) Assignee: NeOnc Technologies, Inc., Los Angeles, CA (US)

( \* ) Notice: Subject to any disclaimer, the term of this patent is extended or adjusted under 35 U.S.C. 154(b) by 0 days. days.

This patent is subject to a terminal disclaimer.

(21) Appl. No.: 14/833,210

(22) Filed: Aug. 24, 2015

(65) Prior Publication Data

US 2015/0359754 A1 Dec. 17, 2015

Related U.S. Application Data

(63) Continuation of application No. 13/993,910, filed as application No. PCT/US2011/065513 on Dec. 16, 2011, now Pat. No. 9,211,269.

(60) Provisional application No. 61/436,365, filed on Jan. 26, 2011, provisional application No. 61/424,332, filed on Dec. 17, 2010.

(51) Int. Cl.
| | | |
|---|---|---|
| C07D 487/04 | (2006.01) |
| A61K 31/4188 | (2006.01) |
| A61P 35/00 | (2006.01) |
| A61K 31/045 | (2006.01) |
| A61K 31/05 | (2006.01) |
| A61K 45/06 | (2006.01) |
| A61K 31/165 | (2006.01) |
| A61K 47/48 | (2006.01) |
| A61K 31/415 | (2006.01) |
| A61K 31/4015 | (2006.01) |
| A61K 31/325 | (2006.01) |
| A61N 5/10 | (2006.01) |
| C07C 271/22 | (2006.01) |
| C07D 231/12 | (2006.01) |
| C07D 207/26 | (2006.01) |

(52) U.S. Cl.
CPC ............ *A61K 31/045* (2013.01); *A61K 31/05* (2013.01); *A61K 31/165* (2013.01); *A61K 31/325* (2013.01); *A61K 31/4015* (2013.01); *A61K 31/415* (2013.01); *A61K 31/4188* (2013.01); *A61K 45/06* (2013.01); *A61K 47/481* (2013.01); *A61K 47/48023* (2013.01); *A61N 5/10* (2013.01); *C07C 271/22* (2013.01); *C07D 207/26* (2013.01); *C07D 231/12* (2013.01); *C07D 487/04* (2013.01); *C07B 2200/07* (2013.01)

(58) Field of Classification Search
CPC .. C07C 35/18; A61K 31/045; A61K 31/4188; C07D 487/04
USPC ........ 514/724, 729, 739, 393; 568/827, 826; 548/303.1
See application file for complete search history.

(56) References Cited

U.S. PATENT DOCUMENTS

| | | | | |
|---|---|---|---|---|
| 8,916,545 B2 * | 12/2014 | Chen | .................... | A61K 31/415 514/80 |
| 2002/0177609 A1 | 11/2002 | Swindell et al. | | |
| 2010/0226913 A1 | 9/2010 | Chen et al. | | |
| 2012/0184560 A1 | 7/2012 | Wong et al. | | |
| 2013/0210877 A1* | 8/2013 | Chen | .................... | A61K 31/415 514/393 |
| 2014/0364471 A1* | 12/2014 | Chen | .................... | A61K 31/415 514/393 |

FOREIGN PATENT DOCUMENTS

| | | |
|---|---|---|
| EP | 1142868 | 10/2001 |
| JP | H09509151 | 9/1997 |
| JP | 2004534520 | 11/2004 |
| JP | 2005518354 | 6/2005 |
| JP | 2007527411 | 9/2007 |
| JP | 2007529414 | 10/2007 |
| JP | 2008535928 | 9/2008 |
| JP | 2009502888 | 1/2009 |
| WO | 199520567 | 8/1995 |
| WO | 200037434 | 6/2000 |
| WO | 2002066662 | 8/2002 |
| WO | 2003043657 | 5/2003 |
| WO | 2004101605 | 11/2004 |
| WO | 2005039496 | 5/2005 |
| WO | 2006110882 | 10/2006 |
| WO | 2007014925 | 2/2007 |
| WO | 2010115491 | 10/2010 |

OTHER PUBLICATIONS

Fernandes et al. Oncol. Rep. 2005, 13 (5), 943-947.*

(Continued)

*Primary Examiner* — Irina Neagu
(74) *Attorney, Agent, or Firm* — Leason Ellis LLP

(57) ABSTRACT

The present invention provides for a method of treating a disease such as cancer, comprising the step of administering to a patient a therapeutically effective amount of an isomer or analog of monoterpene or sesquiterpene (or its derivative), such as an isoperillyl alcohol. The present invention also provides for a method of treating a disease comprising the step of administering to a patient a therapeutically effective amount of a derivative of an isomer or analog of monoterpene or sesquiterpene, such as an isoperillyl alcohol carbamate. The derivative may be an isoperillyl alcohol conjugated with a therapeutic agent such as a chemotherapeutic agent. The route of administration may vary, including inhalation, intranasal, oral, transdermal, intravenous, subcutaneous or intramuscular injection.

9 Claims, 12 Drawing Sheets

(56) References Cited

OTHER PUBLICATIONS

Minitti al. Anticancer Res. 2009, 29 (12), 5171-5185.*
Bhosle et al. Indian Journal of Pharmaceutical Sciences 2006, May-Jun., p. 286-294.*
The Practice of Medicinal Chemistry, updated version, 1st Edition, 1998, p. 297-333.
Yu Zhan, et al., Molecular Biology of Food, China Light Industry Press, 166-167, Sep. 30, 2005.
Encyclopedia of Chemical Engineering, vol. 11, Chemical Industry Press, pp. 228, Aug. 31, 1996.
Chinese Office Action dated Aug. 8, 2017 corresponding to Chinese Application No. 201610009982; 14 pages.
Gold Hoff, et al., "Targeted Inhibition of cyclic AMP pt1osphodiesterase-4 promotes brain tumor regression," Clinical Cancer Research (Dec. 2008), 14(23):7717-7725.

* cited by examiner

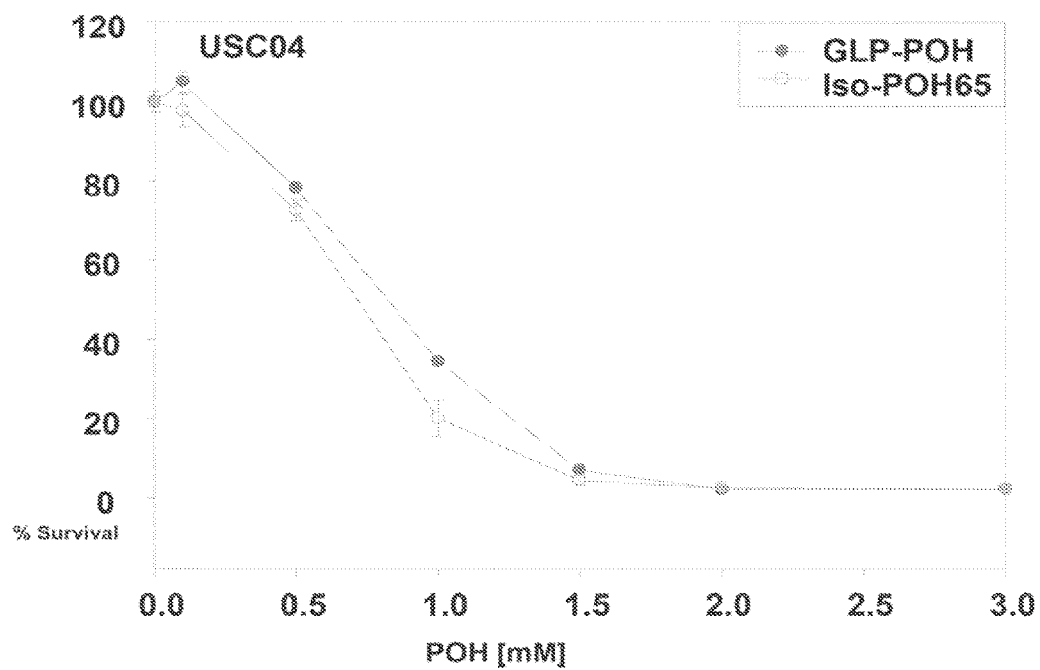

1: Control (no treatment)
2: Sigma-POH 1.5 mM
3: GLP-POH 1.5 mM

4: Control (no treatment)
5: Iso-POH65 1.5 mM
6: Iso-POH79 1.5 mM

METHODS AND DEVICES FOR USING ISOPERILLYL ALCOHOL

CROSS REFERENCE TO RELATED APPLICATION

This application is a continuation of U.S. application Ser. No. 13/993,910, now issued U.S. Pat. No. 9,211,269, filed Aug. 26, 2013, which is a national stage under 35 U.S.C. 371 based on and claiming the benefit of International Application PCT/US11/65513, filed on Dec. 16, 2011, incorporated by reference, which claims the benefit of priority from U.S. Provisional Application Nos. 61/436,365, filed Jan. 26, 2011 and 61/424,332, filed Dec. 17, 2010 the entire contents of each of which are incorporated herein by reference.

FIELD OF THE INVENTION

The present invention relates to isoperillyl alcohol (iso-POH) and isoperillyl alcohol derivatives. Isoperillyl alcohol includes any isomers or analogs of perillyl alcohol. The present invention further relates to methods of using isoperillyl alcohol and isoperillyl alcohol derivatives such as isoperillyl alcohol carbamates to treat cancer.

BACKGROUND OF THE INVENTION

Malignant gliomas, the most common form of central nervous system (CNS) cancers, are currently considered essentially incurable. Among the various malignant gliomas, anaplastic astrocytomas (Grade III) and glioblastoma multiforme (GBM; Grade IV) have an especially poor prognosis due to their aggressive growth and resistance to currently available therapies. The present standard of care for malignant gliomas consists of surgery, ionizing radiation, and chemotherapy. Despite recent advances in medicine, the past 50 years have not seen any significant improvement in prognosis for malignant gliomas. Wen et al. Malignant gliomas in adults. *New England J Med.* 359: 492-507, 2008. Stupp et al. Radiotherapy plus concomitant and adjuvant temozolomide for glioblastoma. *New England J Med.* 352: 987-996, 2005.

The poor response of tumors, including malignant gliomas, to various types of chemotherapeutic agents are often due to intrinsic drug resistance. Additionally, acquired resistance of initially well-responding tumors and unwanted side effects are other problems that frequently thwart long-term treatment using chemotherapeutic agents. Hence, various analogues of chemotherapeutic agents have been prepared in an effort to overcome these problems. The analogues include novel therapeutic agents which are hybrid molecules of at least two existing therapeutic agents. For example, cisplatin has been conjugated with cytotoxic codrugs, or conjugated with bioactive shuttle components such as porphyrins, bile acids, hormones, or modulators that expedite the transmembrane transport or the drug accumulation within the cell. (6-Aminomethylnicotinate)dichloridoplatinum (II) complexes esterified with terpene alcohols were tested on a panel of human tumor cell lines. The terpenyl moieties in these complexes appeared to fulfill a transmembrane shuttle function and increased the rate and extent of the uptake of these conjugates into various tumor cell lines. Schobert et al. Monoterpenes as Drug Shuttles: Cytotoxic (6-minomethylnicotinate)dichloridoplatinum(II) Complexes with Potential To Overcome Cisplatin Resistance. *J. Med. Chem.* 2007, 50, 1288-1293.

Perillyl alcohol (POH), a naturally occurring monoterpene, has been suggested to be an effective agent against a variety of cancers, including CNS cancer, breast cancer, pancreatic cancer, lung cancer, melanomas and colon cancer. Gould, M. Cancer chemoprevention and therapy by monoterpenes. *Environ Health Perspect.* 1997 June; 105 (Suppl 4): 977-979. Hybrid molecules containing both perillyl alcohol and retinoids were prepared to increase apoptosis-inducing activity. Das et al. Design and synthesis of potential new apoptosis agents: hybrid compounds containing perillyl alcohol and new constrained retinoids. *Tetrahedron Letters* 2010, 51, 1462-1466.

In order to improve performance over perillyl alcohol and its derivatives, there is a need to prepare isomers or analogs including isoperillyl alcohol conjugated with other therapeutic agents, and use this material in the treatment of cancers such as malignant gliomas, as well as other brain disorders such as Parkinson's and Alzheimer's disease. These compounds may be administered alone or in combination with other treatment methods including radiation, standard chemotherapy, and surgery. The administration can also be through various routes including intranasal, oral, oral-tracheal for pulmonary delivery, and transdermal.

SUMMARY OF THE INVENTION

The invention provides for a method for treating a disease in a mammal, comprising the step of delivering to the mammal a therapeutically effective amount of an isoperillyl alcohol. The invention also provides for a method for treating a disease in a mammal, comprising the step of delivering to the mammal a therapeutically effective amount of an isoperillyl alcohol carbamate. The method may further comprise the step of treating the mammal with radiation, and/or further comprise the step of delivering to the mammal a chemotherapeutic agent. The diseases treated may be cancer, including a tumor of the nervous system, such as a glioblastoma. The routes of administration include inhalation, intranasal, oral, intravenous, subcutaneous or intramuscular administration.

The present invention further provides for a pharmaceutical composition comprising an isoperillyl alcohol carbamate. The isoperillyl alcohol carbamate may be isoperillyl alcohol conjugated with a therapeutic agent, such as a chemotherapeutic agent. The chemotherapeutic agents that may be used in the present invention include a DNA alkylating agent, a topoisomerase inhibitor, an endoplasmic reticulum stress inducing agent, a platinum compound, an antimetabolite, an enzyme inhibitor, and a receptor antagonist. In certain embodiments, the therapeutic agents are dimethyl celocoxib (DMC), temozolomide (TMZ) or rolipram. The present invention provides for a pharmaceutical composition comprising an isoperillyl alcohol admixed or coformulated with a therapeutic agent. The pharmaceutical compositions of the present invention may be administered before, during or after radiation. The pharmaceutical compositions may be administered before, during or after the administration of a chemotherapeutic agent.

The present invention also provides for a process for making an isoperillyl alcohol carbamate, comprising the step of reacting a first reactant of isoperillyl chloroformate with a second reactant, which may be dimethyl celocoxib (DMC), temozolomide (TMZ) or rolipram. When the second reactant is dimethyl celocoxib, the reaction may be carried out in the presence of acetone and a catalyst of potassium carbonate. When the second reactant is rolipram, the reaction may be carried out in the presence of tetrahydrofuran with n-butyl lithium. The isoperillyl chloroformate may also be prepared by reacting isoperillyl alcohol with phosgene.

| | GC analysis | | | HPLC analysis | | |
|---|---|---|---|---|---|---|
| Sample Ref # | Purity (AUC) | Assay (wt %) | Impurity (RRT: 0.8) | Purity (AUC) | Assay (wt %) | Impurity (RRT: 1.08) |
| SGP-561-65P | 95.8% | NA | 2.1% | NA | NA | NA |
| SGP-561-79P | 93.6% | 97.6% | 0.71% | 98.8% | 104% | 0.73% |

* NA: Not analyzed

Note: Due to the decomposition of the sample by the GC analysis, we have analyzed the Iso-POH by HPLC and compared it with Sigma-Aldrich POH as a standard for wt % assay. Sigma POH is the POH purchased from Sigma Chemicals.

Figure 5A:
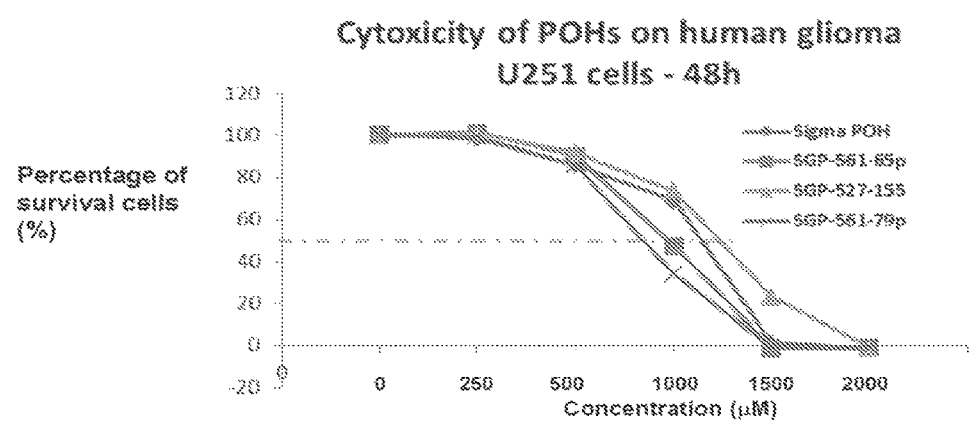
Figure 5B:
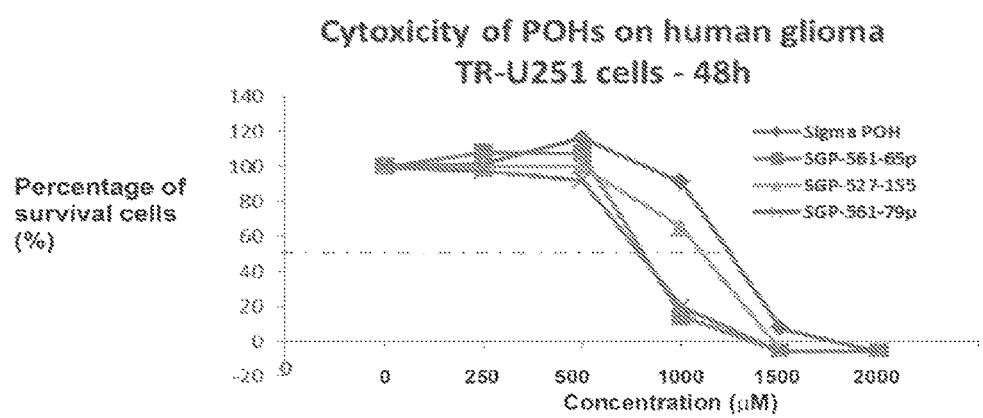

FIGS. 5A and 5B show the results of the MTT cytotoxicity assays demonstrating the efficacy of different types of POH and iso-POH in killing U251 human glioma cells (temozolomide-sensitive) (FIG. 5A) and U251 temozolomide-resistant cells (FIG. 5B).

Figure 6A:
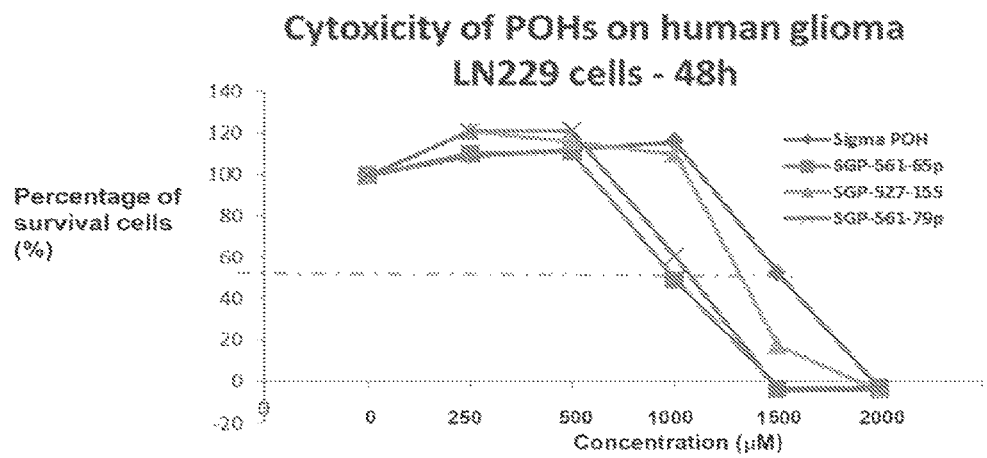
Figure 6B:
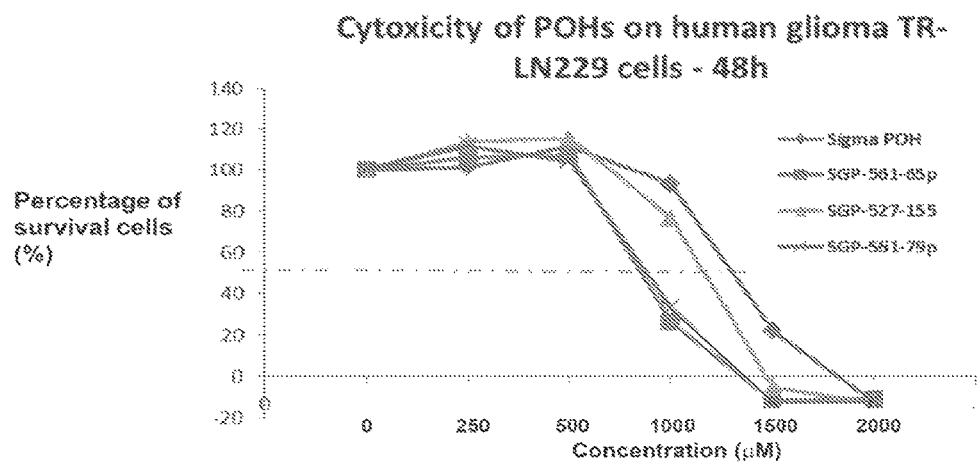

FIGS. 6A and 6B show the results of the MIT cytotoxicity assays demonstrating the efficacy of different types of POH and iso-POH in killing LN229 human glioma cells (temozolomide-sensitive) (FIG. 6A) and LN229 temozolomide-resistant cells (FIG. 6B).

Figure 7A:
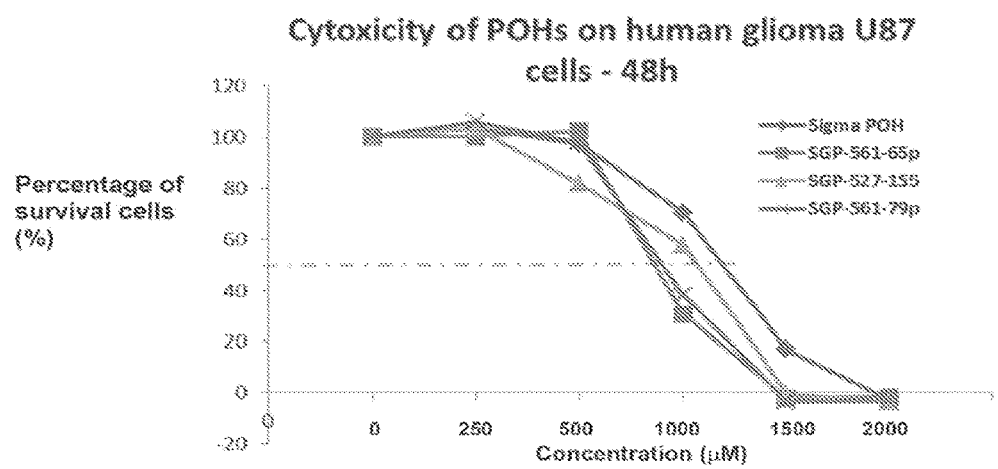
Figure 7B:
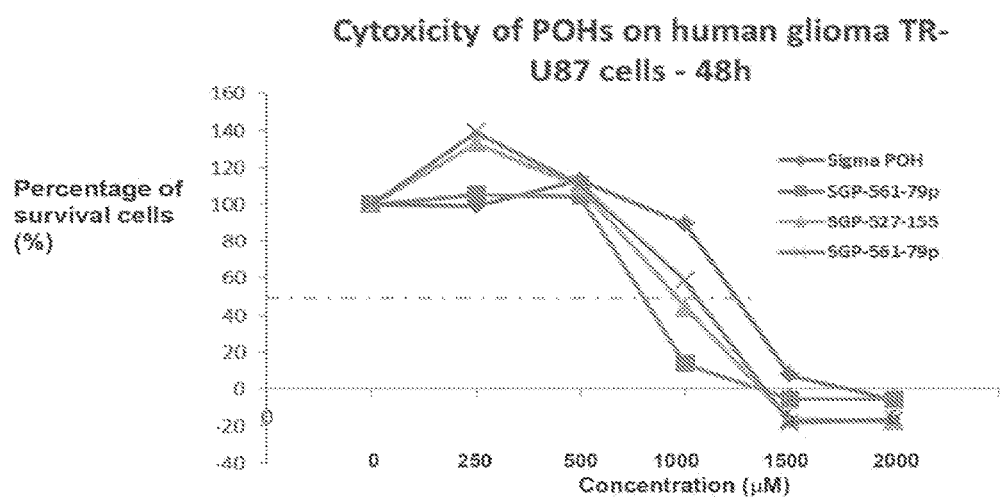

FIGS. 7A and 7B show the results of the MT cytotoxicity assays demonstrating the efficacy of different types of POH and iso-POH in killing U87 human glioma cells (temozolomide-sensitive) (FIG. 7A) and U87 temozolomide-resistant cells (FIG. 7B).

Figure 8A:
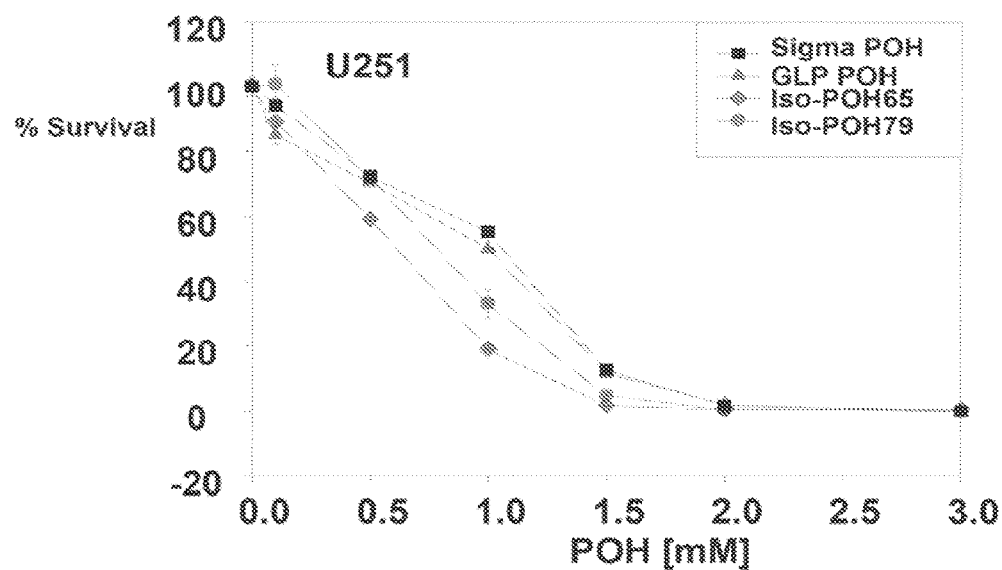
Figure 8B:
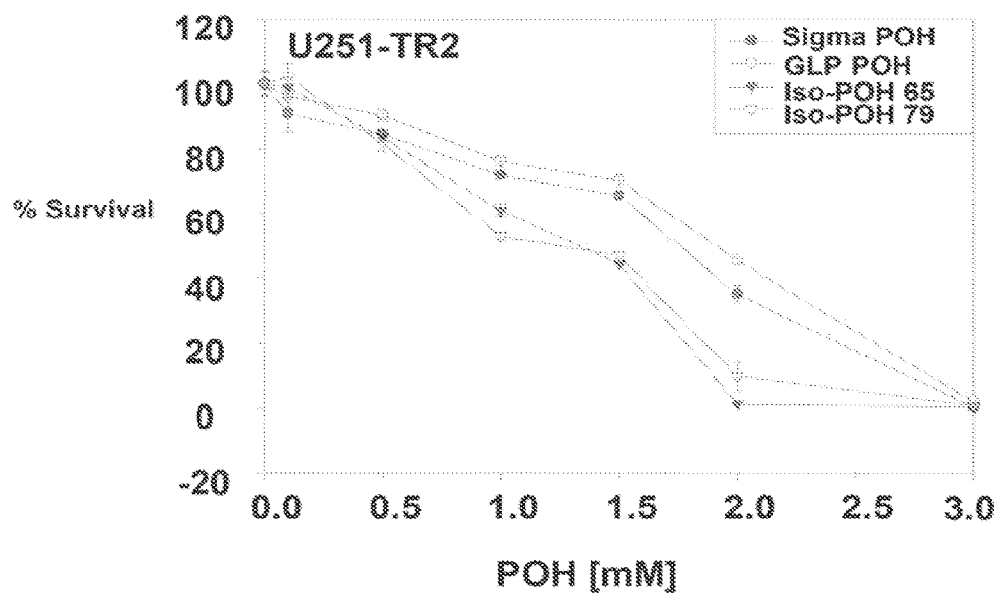
Figure 8C:
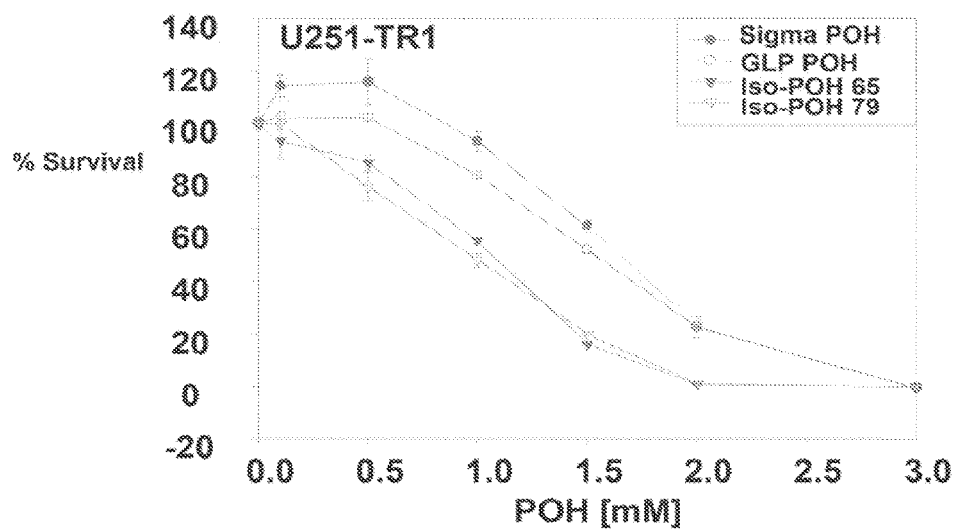

FIGS. 8A, 8B and 8C show the results of the MTT cytotoxicity assays demonstrating the efficacy of different types of POH and iso-POH in killing U251 human glioma cells (temozolomide-sensitive) (FIG. 8A) and U251 temozolomide-resistant cells (FIGS. 88 and 8C). U251-TR1 and U251-TR1 refer to two temozolomide-resistant U251 cell lines. Sigma POH is the POH purchased from Sigma Chemicals. GLP POH is the POH purified to the GLP quality (with a GC relative area purity (area under the curve) of about 98.7%). Iso-POH65 and Iso-POH79 are different batches of iso-POH (see details above for FIGS. 4A and 4B).

FIG. 9 shows the results of the MTT cytotoxicity assays demonstrating the efficacy of POH and iso-POH in killing USC04 glioblastoma cancer stem cell line.

Figure 10A:
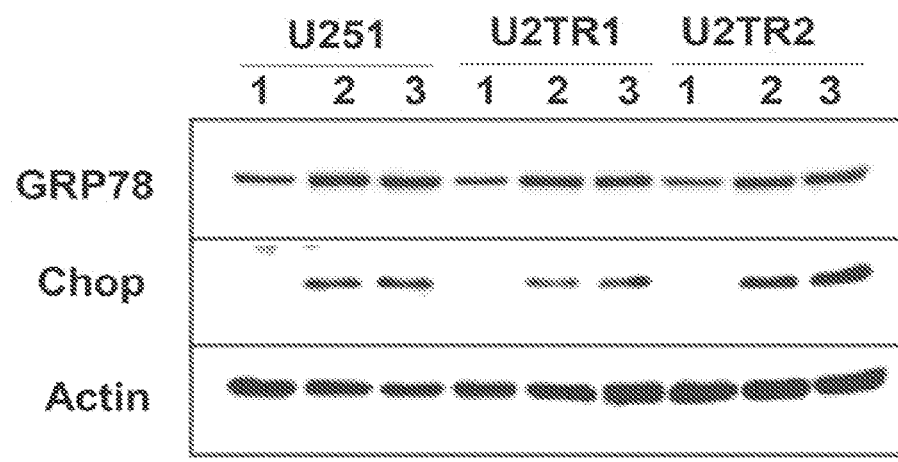
Figure 10B:

FIGS. 10A and 10B show Western blot performed after an 18-hour treatment of U251 glioma cells with Sigma POH (1.5 mM, having a purity of about 95% (AUC)) or ultrapure POH ("GLP-POH", 1.5 mM; having a purity of about 98.7% (AUC)) in both U251 TMZ-sensitive and TMZ-resistant (U251-TR1, U251-TR2) cells demonstrating increased expression of glucose-regulatory protein 78 (GRP-78) and the apoptosis marker CHOP, showing increased endoplasmic reticulum (ER) stress after treatment (FIG. 10A). Under the same conditions, iso-POH (iso-POH65, iso-POH79) also increased ER stress (FIG. 10B).

Figure 11:
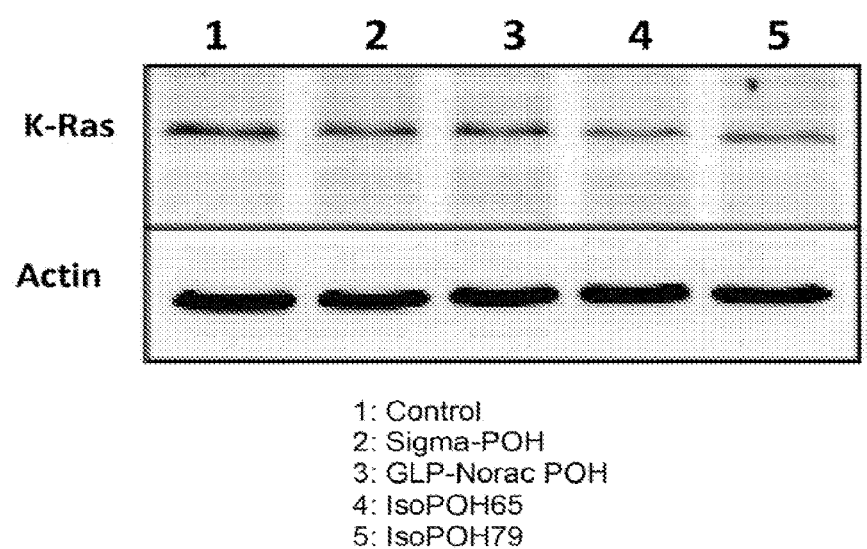

FIG. 11 shows Western blot performed after a 24-hour treatment of U251 glioma cells with 500 μM Sigma POH. GLP POH or iso-POH (isoPOH65, isoPOH79) demonstrating that all treatments decreased Kras expression.

DETAILED DESCRIPTION OF THE INVENTION

The present invention provides for methods of treating a disease such as cancer using an isoperillyl alcohol or a derivative of an isoperillyl alcohol. Routes of administration include inhalation, intranasal, oral, transdermal, intravenous, subcutaneous and intramuscular injection.

In the present methods, a patient is administered a therapeutically effective amount of an isomer or analog of monoterpene or sesquiterpene, such as an isoperillyl alcohol. The present invention also provides for a method of treating a disease comprising the step of administering to a patient a therapeutically effective amount of a derivative of an isomer or analog of monoterpene or sesquiterpene, such as an isoperillyl alcohol carbamate. The derivative may be an isoperillyl alcohol conjugated with a therapeutic agent such as a chemotherapeutic agent.

For example, the isomer or analog of monoterpene or sesquiterpene can be an isoperillyl alcohol (iso-POH). Isoperillyl alcohols include any isomers or analogs of perillyl alcohol. In one embodiment, the isoperillyl alcohol is (4-isopropylidene cyclohex-1-enyl)methanol. Other examples of isoperillyl alcohol include, but are not limited to, (4-isopropyl cyclohexa-1,3-dienyl)methanol, (4-isopropyl cyclohexa-1,4-dienyl)methanol, (4-isopropylphenyl)methanol and (4-isopropenylphenyl)methanol.

An exemplary isoperillyl alcohol, (4-isopropylidene cyclohex-1-enyl)methanol, is shown below:

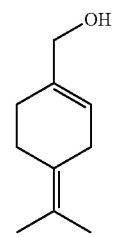

The compounds of the present invention may be used for the treatment of nervous system cancers, such as a malignant glioma (e.g., astrocytoma, anaplastic astrocytoma, glioblastoma multiforme), retinoblastoma, pilocytic astrocytomas (grade I), meningiomas, metastatic brain tumors, neuroblastoma, pituitary adenomas, skull base meningiomas, and skull base cancer. The present invention also provides methods of treating CNS (central nervous system) disorders, including, without limitation, primary degenerative neurological disorders such as Alzheimer's, Parkinson's, psychological disorders, psychosis and depression.

Also encompassed by the present invention is a derivative of an isomer or analog of monoterpene or sesquiterpene, such as an isoperillyl alcohol derivative. For example, the isoperillyl alcohol derivative may be an isoperillyl alcohol carbamate, ester, or ether. The derivative of an isomer or analog of monoterpene or sesquiterpene may be an isomer or analog of monoterpene or sesquiterpene conjugated with a therapeutic agent such as a chemotherapeutic agent. The isoperillyl alcohol derivative may be isoperillyl alcohol conjugated with a therapeutic agent such as a chemotherapeutic agent.

The compounds of the present invention thus include both isomers or analogs of monoterpene or sesquiterpene, and derivatives of an isomer or analog of monoterpene or sesquiterpene. The isomer or analog of monoterpene or sesquiterpene (or the derivative of an isomer or analog of monoterpene or sesquiterpene), may be formulated into a pharmaceutical composition, where the isomer or analog of monoterpene or sesquiterpene (or the derivative of an isomer or analog of monoterpene or sesquiterpene), is present in amounts ranging from about 0.01% (w/w) to about 100% (w/w), from about 0.1% (w/w) to about 80% (w/w), from about 1% (w/w) to about 70% (w/w), from about 10% (w/w) to about 60% (w/w), or from about 0.1% (w/w) to about 20% (w/w). The present compositions can be administered alone, or may be co-administered together with radiation or another agent (e.g., a chemotherapeutic agent), to treat a disease such as cancer. Treatments may be sequential, with isomer or analog of monoterpene or sesquiterpene (or the derivative of an isomer or analog of monoterpene or sesquiterpene) being administered before or after the administration of other agents. For example, an isoperillyl alcohol (or an isoperillyl alcohol carbamate, ester, or ether) may be used to sensitize a cancer patient to radiation or chemotherapy. Alternatively, agents may be administered concurrently. The route of administration may vary, and can include, inhalation, intranasal, oral, transdermal, intravenous, subcutaneous or intramuscular injection.

The compositions of the present invention may contain one or more types of isomers or analogs of monoterpene or sesquiterpene (or the derivatives of isomers or analogs of monoterpene or sesquiterpene). Monoterpenes include terpenes that consist of two isoprene units. Monoterpenes may be linear (acyclic) or contain rings. Derivatives of monoterpenoids are also encompassed by the present invention. Monoterpenoids may be produced by biochemical modifications such as oxidation or rearrangement of monoterpenes. Examples of monoterpenes and monoterpenoids include, perillyl alcohol (S(−)) and (R(+)), ocimene, myrcene, geraniol, citral, citronellol, citronellal, linalool, pinene, terpineol, terpinen, limonene, terpinenes, phellandrenes, terpinolene, terpinen-4-ol (or tea tree oil), pinene, terpineol, terpinen; the terpenoids such as p-cymene which is derived from monocyclic terpenes such as menthol, thymol and carvacrol; bicyclic monoterpenoids such as camphor, borneol and eucalyptol.

Monoterpenes may be distinguished by the structure of a carbon skeleton and may be grouped into acyclic monoterpenes (e.g., myrcene, (Z)- and (E)-ocimene, linalool, geraniol, nerol, citronellol, myrcenol, geranial, citral a, neral, citral b, citronellal, etc.), monocyclic monoterpenes (e.g., limonene, terpinene, phellandrene, terpinolene, menthol, carveol, etc.), bicyclic monoterpenes (e.g., pinene, myrtenol, myrtenal, verbanol, verbanon, pinocarveol, carene, sabinene, camphene, thujene, etc.) and tricyclic monoterpenes (e.g. tricyclene). See *Encyclopedia of Chemical Technology*, Fourth Edition, Volume 23, page 834-835.

Sesquiterpenes of the present invention include terpenes that consist of three isoprene units. Sesquiterpenes may be linear (acyclic) or contain rings. Derivatives of sesquiterpenoids are also encompassed by the present invention. Sesquiterpenoids may be produced by biochemical modifications such as oxidation or rearrangement of sesquiterpenes. Examples of sesquiterpenes include farnesol, farnesal, farnesylic acid and nerolidol. U.S. Provisional Application Nos. 61/310,231 (filed on Mar. 3, 2010), 61/377,747 (filed on Aug. 27, 2010), 61/471,402 (filed on Apr. 4, 2011) and 61/562,105 (filed on Nov. 21, 2011). PCT Application Nos. PTT/US2011/027051 (filed on Mar. 3, 2011) and PCT/US2011/049392 (filed on Aug. 26, 2011). U.S. application Ser. No. 13/040,059 (filed on Mar. 3, 2011). All these applications are incorporated herein by reference in their entirety.

The derivatives of isomers or analogs of monoterpene or sesquiterpene include, but are not limited to, carbamates, esters, ethers, alcohols and aldehydes of the monoterpene (or sesquiterpene). Alcohols may be derivatized to carbamates, esters, ethers, aldehydes or acids.

Carbamate refers to a class of chemical compounds sharing the functional group

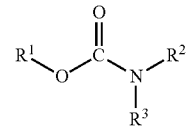

based on a carbonyl group flanked by an oxygen and a nitrogen. $R^1$, $R^2$ and $R^3$ can be a group such as alkyl, aryl, etc., which can be substituted. The R groups on the nitrogen and the oxygen may form a ring. $R^1$—OH may be a monoterpene, e.g., POH. The $R^2$—N—$R^3$ moiety may be a therapeutic agent.

Carbamates may be synthesized by reacting isocyanate and alcohol, or by reacting chloroformate with amine. Carbamates may be synthesized by reactions making use of phosgene or phosgene equivalents. For example, carbamates may be synthesized by reacting phosgene gas, diphosgene or a solid phosgene precursor such as triphosgene with two amines or an amine and an alcohol. Carbamates (also known as urethanes) can also be made from reaction of a urea intermediate with an alcohol. Dimethyl carbonate and diphenyl carbonate are also used for making carbamates. Alternatively, carbamates may be synthesized through the reaction of alcohol and/or amine precursors with an ester-substituted diaryl carbonate, such as bismethylsalicylcarbonate (BMSC). U.S. Patent Publication No. 20100113819.

Carbamates may be synthesized by the following approach:

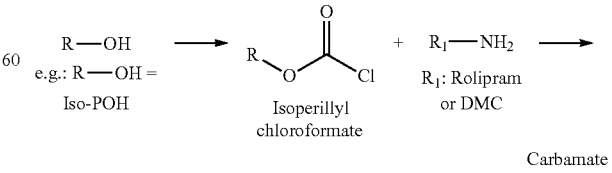

Suitable reaction solvents include, but are not limited to, tetrahydrofuran, dichloromethane, dichloroethane, acetone, and diisopropyl ether. The reaction may be performed at a temperature ranging from about −70° C. to about 80° C., or from about −65° C. to about 50° C. The molar ratio of isoperillyl chloroformate to the substrate R—NH$_2$ may range from about 1:1 to about 2:1, from about 1:1 to about 1.5:1, from about 2:1 to about 1:1, or from about 1.05:1 to about 1.1:1. Suitable bases include, but are not limited to, organic bases, such as triethylamine, potassium carbonate, N,N'-diisopropylethylamine, butyl lithium, and potassium-t-butoxide.

Alternatively, carbamates may be synthesized by the following approach:

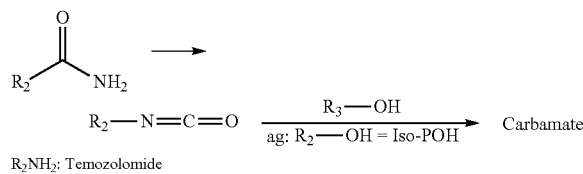

R$_2$NH$_2$: Temozolomide

Suitable reaction solvents include, but are not limited to, dichloromethane, dichloroethane, toluene, diisopropyl ether, and tetrahydrofuran. The reaction may be performed at a temperature ranging from about 25° C. to about 110° C., or from about 30° C. to about 80° C., or about 50° C. The molar ratio of isoperillyl alcohol to the substrate R—N=C=O may range from about 1:1 to about 2:1, from about 1:1 to about 1.5:1, from about 2:1 to about 1:1, or from about 1.05:1 to about 1.1:1.

Esters of the alcohols of the isomers or analogs of monoterpene or sesquiterpene can be derived from an inorganic acid or an organic acid. Inorganic acids include, but are not limited to, phosphoric acid, sulfuric acid, and nitric acid. Organic acids include, but are not limited to, carboxylic acid such as benzoic acid, fatty acid, acetic acid and propionic acid, and any therapeutic agent bearing at least one carboxylic acid functional group. Examples of the esters of alcohols include, but are not limited to, carboxylic acid esters (such as benzoate esters, fatty acid esters (e.g., palmitate ester, linoleate ester, stearate ester, butyryl ester and oleate ester), acetates, propionates (or propanoates), and formates), phosphates, sulfates, and carbamates (e.g., N,N-dimethylaminocarbonyl). Wikipedia—Ester. Retrieved from URL: http://en.wikipedia.org/wiki/Ester.

The derivatives of isoperillyl alcohol include isoperillyl alcohol carbamates, isoperillyl alcohol esters, isoperillic aldehydes, isoperillic acid, isoperillic aldehyde derivatives, and isoperillic acid esters. The derivatives of isoperillyl alcohol may also include its oxidative and nucleophilic/electrophilic addition derivatives. Few examples of derivatives of isoperillyl alcohol are reported in the chemistry literature. See U.S. Pat. No. 5,994,598 and Japanese Patent No. 07048264A.

In certain embodiments, an iso-POH carbamate is synthesized by a process comprising the step of reacting a first reactant of isoperillyl chloroformate with a second reactant such as dimethyl celocoxib (DMC), temozolomide (TMZ) and rolipram. The reaction may be carried out in the presence of tetrahydrofuran and a base such as n-butyl lithium. Isoperillyl chloroformate may be made by reacting iso-POH with phosgene. For example, iso-POH conjugated with temozolomide through a carbamate bond may be synthesized by reacting temozolomide with oxalyl chloride followed by reaction with isoperillyl alcohol. The reaction may be carried out in the presence of 1,2-dichloroethane.

Iso-POH carbamates encompassed by the present invention include, but are not limited to, (3-Methyl 4-oxo-3,4-dihydroimidazo[5,1-d][1,2,3,5]tetrazine-8-carbonyl)-carbamic acid-4-isopropylidene cyclohex-1-enylmethyl ester, 4-(3-Cyclopentyloxy-4-methoxyphenyl)-2-oxo-pyrrolidine-1-carboxylic acid 4-isopropylidene cyclohex-1-enylmethyl ester, 4-(Bis-N,N'-4-isopropylidene cyclohex-1-enylmethyl-oxy carbonyl[5-(2,5-dimethyl phenyl)-3-trifluoromethyl pyrazol-1-yl]benzenesulfonamide. The details of the chemical reactions generating these compounds are described in the Examples below.

In certain embodiments, iso-perillyl alcohol derivatives may be isoperillyl alcohol fatty acid esters, such as palmitoyl ester of iso-POH and linoleoyl ester of iso-POH.

The derivative of an isomer or analog of monoterpene or sesquiterpene may be an isomer or analog of monoterpene or sesquiterpene conjugated with a therapeutic agent. A conjugate encompassed by the present invention is a molecule having an isomer or analog of monoterpene or sesquiterpene covalently bound via a chemical linking group to a therapeutic agent. The molar ratio of the isomer or analog of monoterpene or sesquiterpene to the therapeutic agent in the conjugate may be 1:1, 1:2, 1:3, 1:4, 2:1, 3:1, 4:1, or any other suitable molar ratios. The isomer or analog of monoterpene or sesquiterpene and the therapeutic agent may be covalently linked through carbamate, ester, ether bonds, or any other suitable chemical functional groups. When the isomer or analog of monoterpene or sesquiterpene and the therapeutic agent are conjugated through a carbamate bond, the therapeutic agent may be any agent bearing at least one carboxylic acid functional group, or any agent bearing at least one amine functional group. In a specific example, an isoperillyl alcohol conjugate is isoperillyl alcohol covalently bound via a chemical linking group to a chemotherapeutic agent.

According to the present invention, the therapeutic agents that may be conjugated with an isomer or analog of monoterpene or sesquiterpene include, but are not limited to, chemotherapeutic agents, therapeutic agents for treatment of CNS disorders (including, without limitation, primary degenerative neurological disorders such as Alzheimer's, Parkinson's, multiple sclerosis, Attention-Deficit Hyperactivity Disorder or ADHD, psychological disorders, psychosis and depression), immunotherapeutic agents, angiogenesis inhibitors, and anti-hypertensive agents. Anti-cancer agents that may be conjugated with monoterpene or sesquiterpene can have one or more of the following effects on cancer cells or the subject: cell death; decreased cell proliferation; decreased numbers of cells; inhibition of cell growth; apoptosis; necrosis; mitotic catastrophe; cell cycle arrest; decreased cell size; decreased cell division; decreased cell survival; decreased cell metabolism; markers of cell damage or cytotoxicity; indirect indicators of cell damage or cytotoxicity such as tumor shrinkage; improved survival of a subject; or disappearance of markers associated with undesirable, unwanted, or aberrant cell proliferation. U.S. Patent Publication No. 20080275057.

Also encompassed by the present invention are admixtures and/or coformulations of an isomer or analog of monoterpene or sesquiterpene and at least one therapeutic agent.

Chemotherapeutic agents include, but are not limited to, DNA alkylating agents, topoisomerase inhibitors, endoplasmic reticulum stress inducing agents, a platinum compound, an antimetabolite, vincalkaloids, taxanes, epothilones, enzyme inhibitors, receptor antagonists, tyrosine kinase inhibitors, boron radiosensitizers (i.e. velcade), and chemotherapeutic combination therapies.

Non-limiting examples of DNA alkylating agents are nitrogen mustards, such as Cyclophosphamide (Ifosfamide, Trofosfamide), Chlorambucil (Melphalan, Prednimustine), Bendamustine, Uramustine and Estramustine; nitrosoureas, such as Carmustine (BCNU), Lomustine (Semustine), Fotemustine, Nimustine, Ranimustine and Streptozocin; alkyl sulfonates, such as Busulfan (Mannosulfan, Treosulfan); Aziridines, such as Carboquone, Triaziquone, Triethylenemelamine; Hydrazines (Procarbazine); Triazenes such as Dacarbazine and Temozolomide; Altretamine and Mitobronitol.

Non-limiting examples of Topoisomerase I inhibitors include Campothecin derivatives including SN-38, APC, NPC, campothecin, topotecan, exatecan mesylate, 9-nitro-camptothecin, 9-aminocamptothecin, lurtotecan, rubitecan, silatecan, gimatecan, diflomotecan, extatecan, BN-80927, DX-8951f, and MAG-CPT as described in Pommier Y. (2006) *Nat. Rev. Cancer* 6(10):789-802 and U.S. Patent Publication No. 200510250854; Protoberberine alkaloids and derivatives thereof including berberrubine and coralyne as described in Li et al. (2000) *Biochemistry* 39(24):7107-7116 and Gatto et al. (1996) *Cancer Res.* 15(12):2795-2800; Phenanthroline derivatives including Benzo[i]phenanthridine, Nitidine, and fagaronine as described in Makhey et al. (2003) *Bioorg. Med. Chem.* 11 (8): 1809-1820; Terbenzimidazole and derivatives thereof as described in Xu (1998) *Biochemistry* 37(10):3558-3566; and Anthracycline derivatives including Doxorubicin, Daunorubicin, and Mitoxantrone as described in Foglesong et al. (1992) *Cancer Chemother. Pharmacol.* 30(2):123-]25, Crow et al. (1994) *J. Med. Chem.* 37(19):31913194, and Crespi et al. (1986) *Biochem. Biophys. Res. Commun.* 136(2):521-8. Topoisomerase II inhibitors include, but are not limited to Etoposide and Teniposide. Dual topoisomerase I and II inhibitors include, but are not limited to, Saintopin and other Naphthecenediones, DACA and other Acridine-4-Carboxamindes, Intoplicine and other Benzopyridoindoles, TAS-I03 and other 7H-indeno[2,1-c]Quinoline-7-ones, Pyrazoloacridine, XR 11576 and other Benzophenazines, XR 5944 and other Dimeric compounds, 7-oxo-7H-dibenz[f,ij]Isoquinolines and 7-oxo-7H-benzo[e]pyrimidines, and Anthracenyl-amino Acid Conjugates as described in Denny and Baguley (2003) *Curr. Top. Med. Chem.* 3(3):339-353. Some agents inhibit Topoisomerase II and have DNA intercalation activity such as, but not limited to, Anthracyclines (Aclarubicin, Daunorubicin, Doxorubicin, Epirubicin, Idarubicin, Amrubicin, Pirarubicin, Valrubicin, Zorubicin) and Antracenediones (Mitoxantrone and Pixantrone).

Examples of endoplasmic reticulum stress inducing agents include, but are not limited to, dimethyl-celecoxib (DMC), nelfinavir, celecoxib, and boron radiosensitizers (i.e. velcade (Bortezomib)).

Platinum based compounds are a subclass of DNA alkylating agents. Non-limiting examples of such agents include Cisplatin, Nedaplatin, Oxaliplatin, Triplatin tetranitrate Satraplatin, Aroplatin, Lobaplatin, and JM-216. (see McKeage et al. (1997) *J. Clin. Oncol.* 201:1232-1237 and in general, CHEMOTHERAPY FOR GYNECOLOGICAL NEOPLASM, CURRENT THERAPY AND NOVEL APPROACHES, in the Series Basic and Clinical Oncology, Angioli et al. Eds., 2004).

"FOLFOX" is an abbreviation for a type of combination therapy that is used to treat colorectal cancer. It includes 5-FU, oxaliplatin and leucovorin. Information regarding this treatment is available on the National Cancer Institute's web site, cancer.gov, last accessed on Jan. 16, 2008.

"FOLFOX/BV" is an abbreviation for a type of combination therapy that is used to treat colorectal cancer. This therapy includes 5-FU, oxaliplatin, leucovorin and Bevacizumab. Furthermore, "XELOX/BV" is another combination therapy used to treat colorectal cancer, which includes the prodrug to 5-FU, known as Capecitabine (Xeloda) in combination with oxaliplatin and bevacizumab. Information regarding these treatments are available on the National Cancer Institute's web site, cancer.gov or from 23 the National Comprehensive Cancer Network's web site, nccn.org, last accessed on May 27, 2008.

Non-limiting examples of antimetabolite agents include Folic acid based, i.e. dihydrofolate reductase inhibitors, such as Aminopterin, Methotrexate and Pemetrexed; thymidylate synthase inhibitors, such as Raltitrexed, Pemetrexed; Purine based, i.e. an adenosine deaminase inhibitor, such as Pentostatin, a thiopurine, such as Thioguanine and Mercaptopurine, a halogenated/ribonucleotide reductase inhibitor, such as Cladribine, Clofarabine, Fludarabine, or a guanine/guanosine: thiopurine, such as Thioguanine; or Pyrimidine based, i.e. cytosine/cytidine: hypomethylating agent, such as Azacitidine and Decitabine, a DNA polymerase inhibitor, such as Cytarabine, a ribonucleotide reductase inhibitor, such as Gemcitabine, or a thymine/thymidine: thymidylate synthase inhibitor, such as a Fluorouracil (5-FU). Equivalents to 5-FU include prodrugs, analogs and derivative thereof such as 5'-deoxy-5-fluorouridine (doxifluroidine), 1-tetrahydrofuranyl-5-fluorouracil (ftorafur), Capecitabine (Xeloda), S-I (MBMS-247616, consisting of tegafur and two modulators, a 5-chloro-2,4-dihydroxypyridine and potassium oxonate), ralititrexed (tomudex), nolatrexed (Thymitaq, AG337), LY231514 and ZD9331, as described for example in Papamicheal (1999) *The Oncologist* 4:478-487.

Examples of vincalkaloids, include, but are not limited to Vinblastine, Vincristine, Vinflunine, Vindesine and Vinorelbine.

Examples of taxanes include, but are not limited to docetaxel, Larotaxel, Ortataxel, Paclitaxel and Tesetaxel. An example of an epothilone is iabepilone.

Examples of enzyme inhibitors include, but are not limited to farnesyltransferase inhibitors (Tipifarnib); CDK inhibitor (Alvocidib, Seliciclib); proteasome inhibitor (Bortezomib); phosphodiesterase inhibitor (Anagrelide; rolipram); IMP dehydrogenase inhibitor (Tiazofurine); and lipoxygenase inhibitor (Masoprocol). Examples of receptor antagonists include, but are not limited to ERA (Atrasentan); retinoid X receptor (Bexarotene); and a sex steroid (Testolactone).

Examples of tyrosine kinase inhibitors include, but are not limited to inhibitors to ErbB: HER1/EGFR (Erlotinib, Gefitinib, Lapatinib, Vandetanib, Sunitinib, Neratinib); HER2/neu (Lapatinib, Neratinib); RTK class III: C-kit (Axitinib, Sunitinib, Sorafenib), FLT3 (Lestaurtinib), PDGFR (Axitinib, Sunitinib, Sorafenib); and VEGFR (Vandetanib, Semaxanib, Cediranib, Axitinib, Sorafenib); bcr-abl (Imatinib, Nilotinib, Dasatinib); Src (Bosutinib) and Janus kinase 2 (Lestaurtinib).

"Lapatinib" (Tykerb®) is a dual EGFR and erbB-2 inhibitor. Lapatinib has been investigated as an anticancer monotherapy, as well as in combination with trastuzumab, capecitabine, letrozole, paclitaxel and FOLFIRI (irinotecan, 5-fluorouracil and leucovorin), in a number of clinical trials. It is currently in phase III testing for the oral treatment of metastatic breast, head and neck, lung, gastric, renal and bladder cancer.

A chemical equivalent of lapatinib is a small molecule or compound that is a tyrosine kinase inhibitor (TKI) or alternatively a HER-1 inhibitor or a HER-2 inhibitor. Several TKIs have been found to have effective antitumor activity and have been approved or are in clinical trials. Examples of such include, but are not limited to, Zactima (ZD6474), Iressa (gefitinib), imatinib mesylate (STI571; Gleevec), erlotinib (OSI-1774; Tarceva), canertinib (CI 1033), semaxinib (SUM 16), vatalanib (PTK787/ZK222584), sorafenib (BAY 43-9006), sutent (SUI 1248) and lefltmomide (SU101).

PTK/ZK is a tyrosine kinase inhibitor with broad specificity that targets all VEGF receptors (VEGFR), the platelet-derived growth factor (PDGF) receptor, c-KIT and c-Fms. Drevs (2003) Idrugs 6(8):787-794. PTK/ZK is a targeted drug that blocks angiogenesis and lymphangiogenesis by inhibiting the activity of all known receptors that bind VEGF including VEGFR-1 (Flt-1), VEGFR-2 (KDR/Flk-1) and VEGFR-3 (Fit-4). The chemical names of PTK/ZK are 1-[4-Chloroanilino]-4-[4-pyridylmethyl]phthalazine Succinate or 1-Phthalazinamine, N-(4-chlorophenyl)-4-(4-pyridinylmethyl)-butanedioate (1:1). Synonyms and analogs of PTK/TK are known as Vatalanib, CGP79787D, PTK787/ZK 222584, CGP-79787, DE-00268, PTK-787, PTK787A, VEGFR-TK inhibitor, ZK 222584 and ZK.

Chemotherapeutic agents that can be used in admixtures and/or coformulations and/or conjugated with an isomer or analog of monoterpene or sesquiterpene may also include amsacrine, Trabectedin, retinoids (Alitretinoin, Tretinoin), Arsenic trioxide, asparagine depleter Asparaginase/Pegaspargase), Celecoxib, Demecolcine. Elesclomol, Elsamitrucin, Etoglucid, Lonidamine, Lucanthone, Mitoguazone, Mitotane, Oblimersen, Temsirolimus, and Vorinostat.

An isomer or analog of monoterpene or sesquiterpene may be conjugated and/or used in admixtures and/or coformulations with angiogenesis inhibitors. Examples of angiogenesis inhibitors include, but are not limited to, angiostatin, angiozyme, antithrombin III, AG3340, VEGF inhibitors, batimastat, bevacizumab (avastin), BMS-275291, CAI, 2C3, HuMV833 Canstatin, Captopril, carboxyamidotriazole, cartilage derived inhibitor (CDI), CC-5013, 6-O-(chloroacetyl-carbonyl)-fumagillol, COL-3, combretastatin, combretastatin A4 Phosphate, Dalteparin, EMD 121974 (Cilengitide), endostatin, erlotinib, gefitinib (Iressa), genistein, halofuginone hydrobromide, Id1, Id3, IM862, imatinib mesylate, IMC-IC11 Inducible protein 10, interferon-alpha, interleukin 12, lavendustin A, LY317615 or AE-941, marimastat, mspin, medroxpregesterone acetate, Meth-1, Meth-2, 2-methoxyestradiol (2-ME), neovastat, oteopontin cleaved product, PEX, pigment epithelium growth factor (PEGF), platelet factor 4, prolactin fragment, proliferin-related protein (PRP), PTK787/ZK 222584, ZD6474, recombinant human platelet factor 4 (rPF4), restin, squalamine, SU5416, SU6668, SU11248 suramin, Taxol, Tecogalan, thalidomide, thrombospondin, TNP-470, troponin-1, vasostatin, VEG1, VEGF-Trap, and ZD6474.

Non-limiting examples of angiogenesis inhibitors also include, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, pentosan polysulfate, angiotensin II antagonists, cyclooxygenase inhibitors (including non-steroidal anti-inflammatory drugs (NSAIDs) such as aspirin and ibuprofen, as well as selective cyclooxygenase-2 inhibitors such as celecoxib and rofecoxib), and steroidal anti-inflammatories (such as corticosteroids, mineralocorticoids, dexamethasone, prednisone, prednisolone, methylpred, betamethasone).

Other therapeutic agents that modulate or inhibit angiogenesis and may also be conjugated and/or admixed and/or coformulated with an isomer or analog of monoterpene or sesquiterpene include agents that modulate or inhibit the coagulation and fibrinolysis systems, including, but not limited to, heparin, low molecular weight heparins and carboxypeptidase U inhibitors (also known as inhibitors of active thrombin activatable fibrinolysis inhibitor [TAFIa]). U.S. Patent Publication No. 20090328239. U.S. Pat. No. 7,638,549.

Non-limiting examples of the anti-hypertensive agents include angiotensin converting enzyme inhibitors (e.g., captopril, enalapril, delapril etc.), angiotensin 11 antagonists (e.g., candesartan cilexetil, candesartan, losartan (or Cozaar), losartan potassium, eprosartan, valsartan (or Diovan), termisartan, irbesartan, tasosartan, olmesartan, olmesartan medoxomil etc.), calcium antagonists (e.g., manidipine, nifedipine, amlodipine (or Amlodin), efonidipine, nicardipine etc.), diuretics, renin inhibitor (e.g., aliskiren etc.), aldosterone antagonists (e.g., spironolactone, eplerenone etc.), beta-blockers (e.g., metoprolol (or Toporol), atenolol, propranolol, carvedilol, pindolol etc.), vasodilators (e.g., nitrate, soluble guanylate cyclase stimulator or activator, prostacycline etc.), angiotensin vaccine, clonidine and the like. U.S. Patent Publication No. 20100113780.

Other therapeutic agents that may be conjugated and/or admixed and/or coformulated with an isomer or analog of monoterpene or sesquiterpene include, but are not limited to, Sertraline (Zoloft), Topiramate (Topamax), Duloxetine (Cymbalta), Sumatriptan (Imitrex), Pregabalin (Lyrica), Lamotrigine (Lamictal), Valaciclovir (Valtrex), Tamsulosin (Flomax), Zidovudine (Combivir), Lamivudine (Combivir), Efavirenz (Sustiva), Abacavir (Epzicom), Lopinavir (Kaletra), Pioglitazone (Actos), Desloratidine (Clarinex), Cetirizine (Zyrtec), Pentoprazole (Protonix), Lansoprazole (Prevacid), Rebeprazole (Aciphex), Moxifloxacin (Avelox), Meloxicam (Mobic), Dorzolamide (Truspot), Diclofenac (Voltaren), Enlapril (Vasotec), Montelukast (Singulair), Sildenafil (Viagra), Carvedilol (Coreg), Ramipril (Delix).

Table 1 lists pharmaceutical agents that can be conjugated with an isomer or analog of monoterpene or sesquiterpene, including the structure of the pharmaceutical agent and the preferred derivative for conjugation.

TABLE 1

| Brand Name | Generic Name | Activity | Structure | Preferred Derivative |
|---|---|---|---|---|
| Zoloft | Sertaline | Depression | 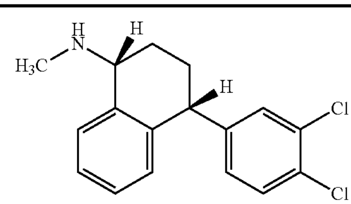 | Carbamate |

TABLE 1-continued
| Brand Name | Generic Name | Activity | Structure | Preferred Derivative |
|---|---|---|---|---|
| Topamax | Topiramate | Seizures | 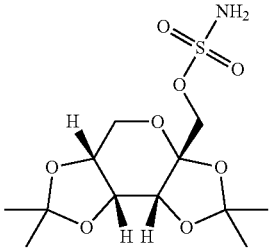 | Carbamate |
| Cymbalta | Duloxetine | Depression | 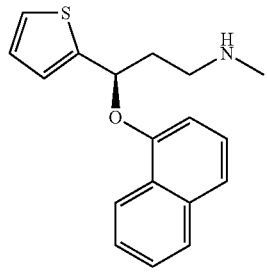 [SMILES: CNCC[C@@H](Oc1cccc2ccccc12)c1cccs1] | Carbamate |
| Imitrex | Sumatriptan | Migraine | 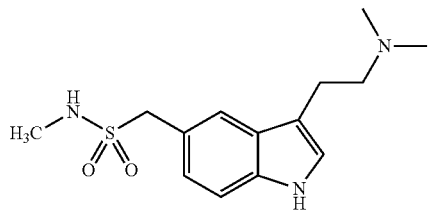 | Carbamate |
| Lyrica | Pregabalin | Neuropathic pain | 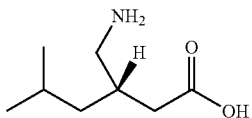 | Carbamate or Ester |
| Lamictal | Lamotrigine | Seizures | 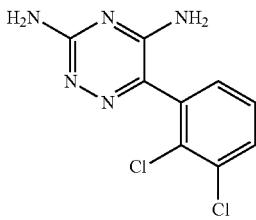 [SMILES: Nc1nnc(-c2cccc(Cl)c2Cl)c(N)n1] | Carbamate |
| Valtrex | Valaciclovir | Herpes | 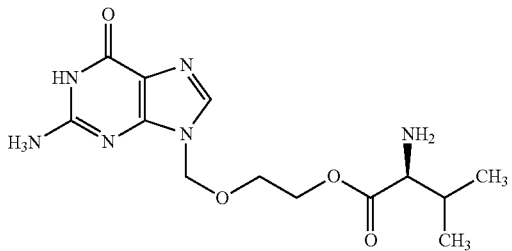 [SMILES: CC(C)[C@H](N)C(=O)OCCOCn1cnc2c(=O)[nH]c(N)nc21] | Carbamate |

TABLE 1-continued

| Brand Name | Generic Name | Activity | Structure | Preferred Derivative |
|---|---|---|---|---|
| Tarceva | Erlotinib | Non-small cell lung cancer | 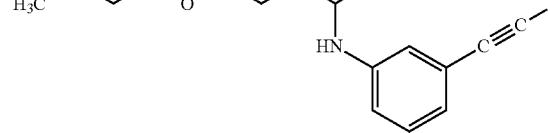 | Carbamate |
| Flomax | Tamsulosin | Benign prostatic Cancer | 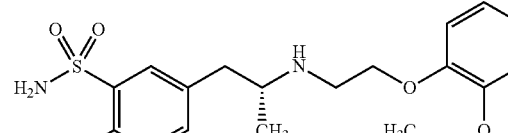 | Carbamate |
| Gleevec | Imatinib | Leukemia | 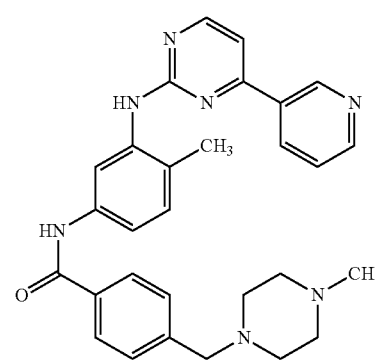 | Carbamate |
| Combivir | Zidovudine | HIV infection | 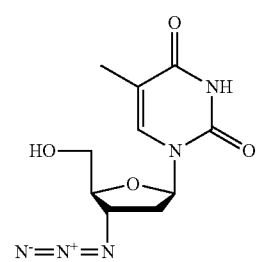 | Carbamate |
| Combivir | Lamivudine | HIV infection | 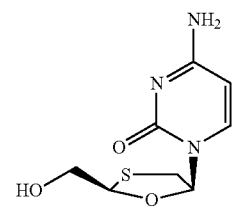 [SMILES: Nc1ccn([C@@H]2CS[C@H](CO)O2)c(=O)n1] | Carbamate |
| Sustiva | Efavirenz | HIV infection | 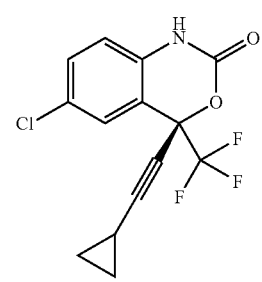 [SMILES: O=C1Nc2ccc(Cl)cc2[C@@](C#CC2CC2)(C(F)(F)F)O1] | Carbamate |

US 9,987,237 B2

TABLE 1-continued

| Brand Name | Generic Name | Activity | Structure | Preferred Derivative |
|---|---|---|---|---|
| Epzicom | Abacavir | HIV infection | 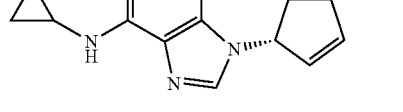 | Carbamate |
| Kaletra | Lopinavir | HIV infection | 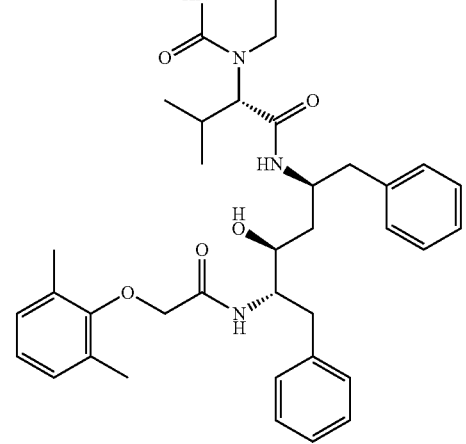 | Carbamate |
| Actos | Pioglitazone | Type-2 diabetes | 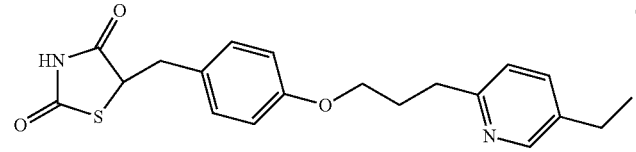 [SMILES: CCc1ccc(CCCOc2ccc(CC3SC(=O)NC3=O)cc2)nc1] | Carbamate |
| Clarinex | Desloratidine | Allergeric rhinitis | 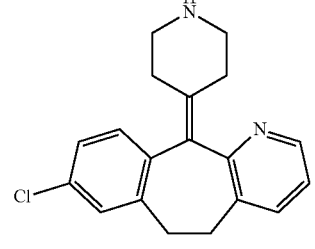 | Carbamate |
| Zyrtec | Cetirizine | Allergic | 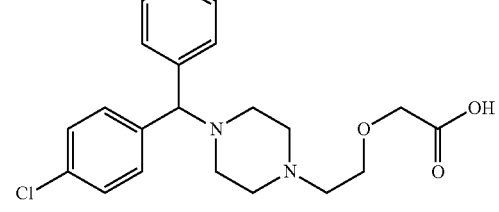 | Ester |
| Protonix | Pentoprazole | Gastrointestinal | 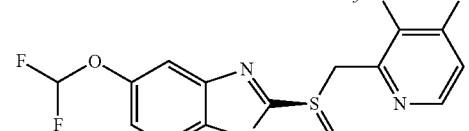 | Carbamate |

TABLE 1-continued

| Brand Name | Generic Name | Activity | Structure | Preferred Derivative |
|---|---|---|---|---|
| Prevacid | Lansoprazole | Gastrointestinal | 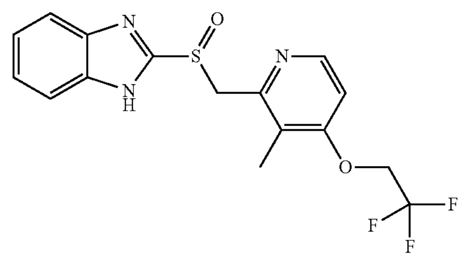 [SMILES: Cc1c(OCC(F)(F)F)ccnc1CS(=O)c1nc2ccccc2[nH]1] | Carbamate |
| Aciphex | Rebeprazole | Gastrointestinal | 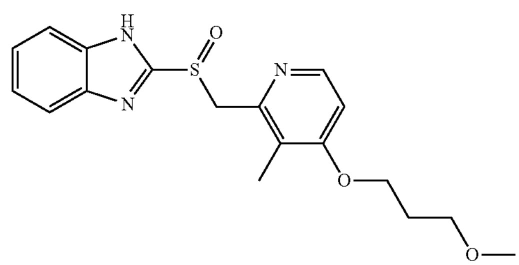 [SMILES: COCCCOc1ccnc(CS(=O)c2nc3ccccc3[nH]2)c1C] | Carbamate |
| Diovan | Valsartan | Hypertension | 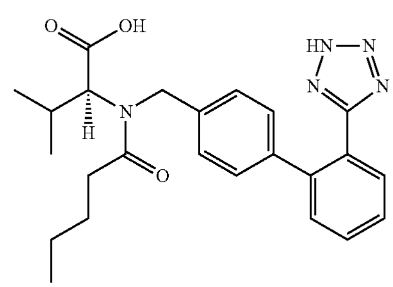 [SMILES: CCCCC(=O)N(Cc1ccc(-c2ccccc2-c2nn[nH]n2)cc1)[C@H](C(=O)O)C(C)C] | Carbamate |
| Cozaar | Losartan | Hypertension | 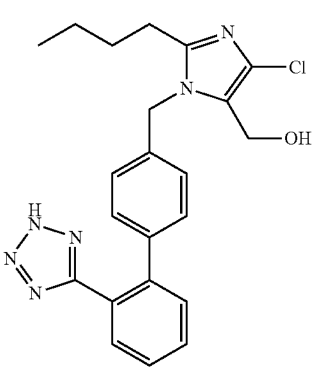 [SMILES: CCCCc1nc(Cl)c(CO)n1Cc1ccc(-c2ccccc2-c2nn[nH]n2)cc1] | Carbamate |
| Avelox | Moxifloxacin | Bacterial infection | 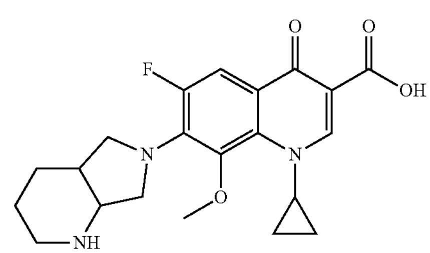 [SMILES: COc1c(N2CC3CCCNC3C2)c(F)cc2c(=O)c(C(=O)O)cn(C3CC3)c12] | Carbamate or Ester |

TABLE 1-continued

| Brand Name | Generic Name | Activity | Structure | Preferred Derivative |
|---|---|---|---|---|
| Mobic | Meloxicam | Osteroarthritis | 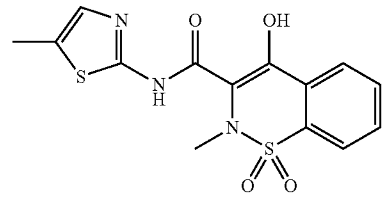 [SMILES: Cc1cnc(NC(=O)C2=C(O)c3ccccc3S(=O)(=O)N2C)s1] | Carbamate |
| Truspot | Dorzolamide | Intraocular pressure | 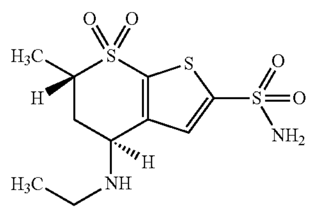 [SMILES: CCN[C@H]1C[C@H](C)S(=O)(=O)c2sc(S(N)(=O)=O)cc21] | Carbamate |
| Voltraren | Diclofenac | Osteoarthritis & rheumatoid arthritis | 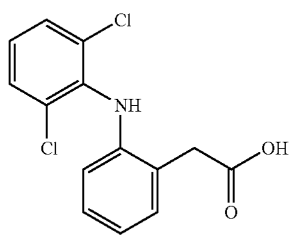 [SMILES: O=C(O)Cc1ccccc1Nc1c(Cl)cccc1Cl] | Carbamate or Ester |
| Vasotec | Enlapril | Hypertension | 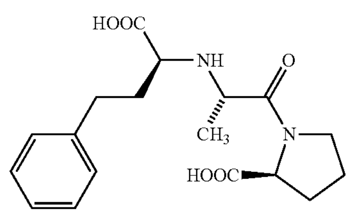 [SMILES: C[C@H](N[C@@H](CCc1ccccc1)C(=O)O)C(=O)N1CCC[C@H]1C(=O)O] | Carbamate or Ester |
| Singulair | Montelukast | Asthma | 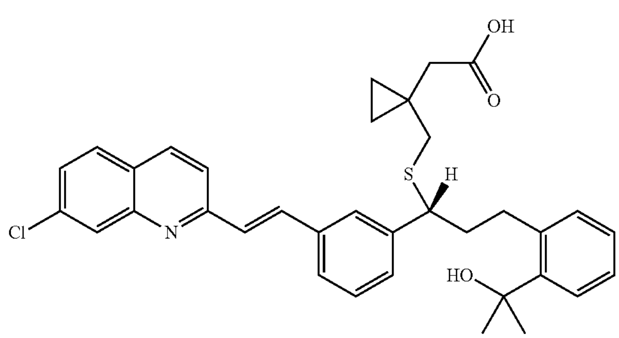 [SMILES: CC(C)(O)c1ccccc1CC[C@@H](SCC1(CC(=O)O)CC1)c1cccc(/C=C/c2ccc3ccc(Cl)cc3n2)c1] | Ester |
| Amlodin | Amlodipine | Hypertension | 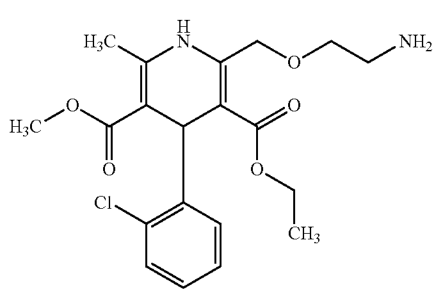 [SMILES: CCOC(=O)C1=C(COCCN)NC(C)=C(C(=O)OC)C1c1ccccc1Cl] | Carbamate |

TABLE 1-continued

| Brand Name | Generic Name | Activity | Structure | Preferred Derivative |
|---|---|---|---|---|
| Toporol | Metoprolol | Hypertension | 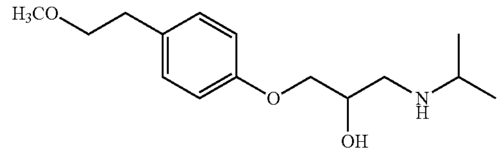 [SMILES: COCCc1ccc(OCC(O)CNC(C)C)cc1] | Carbamate |
| Viagra | Sildenafil | Erectile dysfunction | 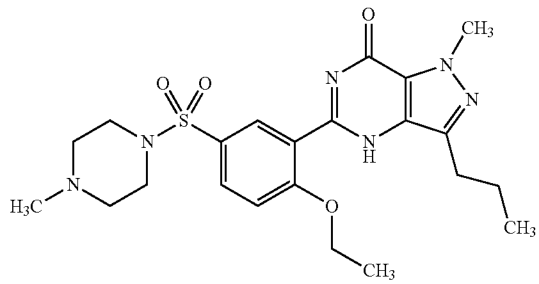 [SMILES: CCCc1nn(C)c2c(=O)nc(-c3cc(S(=O)(=O)N4CCN(C)CC4)ccc3OCC)[nH]c12] | Carbamate |
| Coreg | Carvedilol | Hypertension | 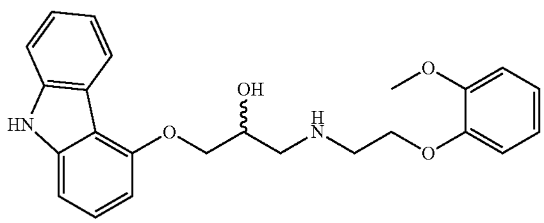 [SMILES: COc1ccccc1OCCNCC(O)COc1cccc2[nH]c3ccccc3c12] | Carbamate |
| Delix | Ramipril | Hypertension | 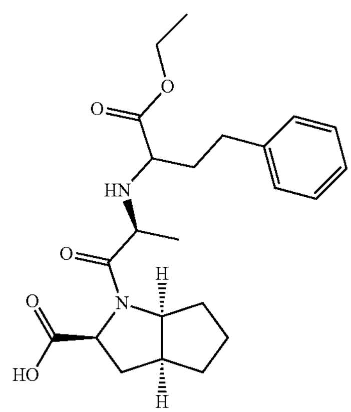 [SMILES: CCOC(=O)C(CCc1ccccc1)N[C@@H](C)C(=O)N1[C@H](C(=O)O)C[C@@H]2CCC[C@@H]21] | Carbamate or Ester |
| Sinemet (Parcopa, Atamet) | L-DOPA | Neurological disorders | 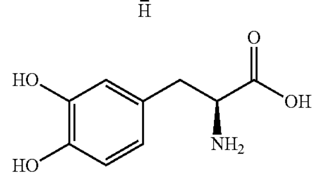 | |

By way of example, an L-DOPA iso-POH conjugate is shown below:

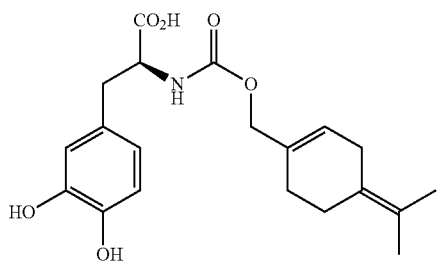 [SMILES: CC(C)=C1CC=C(COC(=O)N[C@@H](Cc2ccc(O)c(O)c2)C(=O)O)CC1]

The purity of an isomer or analog of monoterpene or sesquiterpene, or its derivatives, may be assayed by gas chromatography (GC) or high pressure liquid chromatography (HPLC). Other techniques for assaying the purity of the compounds of the present invention and for determining the presence of impurities include, but are not limited to, nuclear magnetic resonance (NMR) spectroscopy, mass spectrometry (MS). GC-MS, infrared spectroscopy (IR), and thin layer chromatography (TLC). Chiral purity can be assessed by chiral GC or measurement of optical rotation.

The isomer or analog of monoterpene or sesquiterpene (or its derivatives), may be purified by methods such as crystallization, or by separating the isomer or analog of monoterpene or sesquiterpene (or its derivative), from impurities according to the unique physicochemical properties (e.g., solubility or polarity) of the isomer or analog of monoterpene or sesquiterpene (or its derivative). Accordingly, the isomer or analog of monoterpene or sesquiterpene (or its derivative) can be separated by suitable separation techniques known in the art, such as preparative chromatography, (fractional) distillation, or (fractional) crystallization.

The invention also provides for methods of using an isomer or analog of monoterpene or sesquiterpene, as well as using a derivative of an isomer or analog of monoterpene or sesquiterpene, to treat a disease, such as cancer or other nervous system disorders. The compounds of the present invention may be administered alone, or in combination with radiation, surgery or chemotherapeutic agents. An isomer or analog of monoterpene or sesquiterpene, or its derivative, may also be co-administered with antiviral agents, anti-inflammatory agents or antibiotics. The agents may be administered concurrently or sequentially. The compounds of the present invention can be administered before, during or after the administration of the other active agent(s).

The compounds and methods of the present invention may used to inhibit the Ras protein. The Ras family is a protein family of small GTPases that are involved in cellular signal transduction. Activation of Ras signaling causes cell growth, differentiation and survival. Mtations in ras genes can permanently activate it and cause inappropriate transmission inside the cell even in the absence of extracellular signals. Because these signals result in cell growth and division, dysregulated Ras signaling can ultimately lead to oncogenesis and cancer. Activating mutations in Ras are found in 20-25% of all human tumors and up to 90% in specific tumor types. Goodsell D S (1999). Downward J., "The molecular perspective: the ras oncogene". *Oncologist* 4 (3): 263-4. (January 2003). "Targeting RAS signalling pathways in cancer therapy". *Nat Rev. Cancer* 3 (1): 11-22. Ras family members include, but are not limited to, HRAS; KRAS; NRAS; DIRAS1; DIRAS2; DIRAS3; ERAS; GEM; MRAS; NKIRAS1; NKIRAS2; NRAS; RALA; RALB; RAP1A; RAP1B; RAP2A; RAP2B; RAP2C; RASD1; RASD2; RASL10A; RASL10B; RASL11A; RASL11B; RASL12; REM1; REM2; RERG; RERGL; RRAD; RRAS; and RRAS. Wennerberg K, Rossman K L, Der C J (March 2005). "The Ras superfamily at a glance". *J. Cell. Sci.* 118 (Pt 5): 843-6.

The isomer or analog of monoterpene or sesquiterpene, or a derivative of the isomer or analog of monoterpene or sesquiterpene, may be used in combination with radiation therapy. In one embodiment, the present invention provides for a method of treating tumor cells, such as malignant glioma cells, with radiation, where the cells are treated with an effective amount of an isomer or analog of monoterpene or sesquiterpene (or its derivative), such as isoperillyl alcohol, and then exposed to radiation. Treatment by the compounds of the present invention may be before, during and/or after radiation. For example, the compounds of the present invention may be administered continuously beginning one week prior to the initiation of radiotherapy and continued for two weeks after the completion of radiotherapy. U.S. Pat. Nos. 5,587,402 and 5,602,184.

In one embodiment, the present invention provides for a method of treating tumor cells, such as malignant glioma cells, with chemotherapy, where the cells are treated with an effective amount of an isomer or analog of monoterpene or sesquiterpene (or a derivative of the isomer or analog of monoterpene or sesquiterpene), such as isoperillyl alcohol, and then exposed to chemotherapy. Treatment by the compounds of the present invention may be before, during and/or after chemotherapy.

The compounds of the present invention may be used for the treatment of nervous system cancers, such as a malignant glioma (e.g., astrocytoma, anaplastic astrocytoma, glioblastoma multiforme), retinoblastoma, pilocytic astrocytomas (grade I), meningiomas, metastatic brain tumors, neuroblastoma, pituitary adenomas, skull base meningiomas, and skull base cancer. As used herein, the term "nervous system tumors" refers to a condition in which a subject has a malignant proliferation of nervous system cells.

Cancers that can be treated by the present compounds include, but are not limited to, lung cancer, ear, nose and throat cancer, leukemia, colon cancer, melanoma, pancreatic cancer, mammary cancer, prostate cancer, breast cancer, hematopoietic cancer, ovarian cancer, basal cell carcinoma, biliary tract cancer; bladder cancer; bone cancer; breast cancer; cervical cancer; choriocarcinoma; colon and rectum cancer; connective tissue cancer; cancer of the digestive system; endometrial cancer, esophageal cancer; eye cancer; cancer of the head and neck; gastric cancer; intra-epithelial neoplasm; kidney cancer; larynx cancer; leukemia including acute myeloid leukemia, acute lymphoid leukemia, chronic myeloid leukemia, chronic lymphoid leukemia; liver cancer; lymphoma including Hodgkin's and Non-Hodgkin's lymphoma; myeloma; fibroma, neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas. U.S. Pat. No. 7,601,355.

The present invention also provides methods of treating CNS disorders, including, without limitation, primary degenerative neurological disorders such as Alzheimer's, Parkinson's, psychological disorders, psychosis and depression. Autism may also be treated by the present compositions and methods. Treatment may consist of the use of a compound of the present invention alone or in combination with current medications used in the treatment of Parkinson's, Alzheimer's, or psychological disorders.

The present invention also provides a method of improving immunomodulatory therapy responses comprising the steps of exposing cells to an effective amount of a compound of the present invention, such as isoperillyl alcohol, before or during immunomodulatory treatment. Preferred immunomodulatory agents are cytokines, such interleukins, lymphokines, monokines, interfereons and chemokines.

The present composition may be administered by any method known in the art, including, without limitation, intranasal, oral, transdermal, ocular, intraperitoneal, inhalation, intravenous, ICV, intracisternal injection or infusion, subcutaneous, implant, vaginal, sublingual, urethral (e.g., urethral suppository), subcutaneous, intramuscular, intravenous, rectal, sub-lingual, mucosal, ophthalmic, spinal, intrathecal, intra-articular, intra-arterial, sub-arachinoid, bronchial and lymphatic administration. Topical formulation may be in the form of gel, ointment, cream, aerosol, etc; intranasal formulation can be delivered as a spray or in a drop; transdermal formulation may be administered via a transdermal patch or iontorphoresis; inhalation formulation can be delivered using a nebulizer or similar device. Compositions can also take the form of tablets, pills, capsules, semisolids, powders, sustained release formulations, solutions, suspensions, elixirs, aerosols, or any other appropriate compositions.

To prepare such pharmaceutical compositions, one or more of compound of the present invention may be mixed with a pharmaceutical acceptable carrier, adjuvant and/or excipient, according to conventional pharmaceutical compounding techniques. Pharmaceutically acceptable carriers that can be used in the present compositions encompass any of the standard pharmaceutical carriers, such as a phosphate buffered saline solution, water, and emulsions, such as an oil/water or water/oil emulsion, and various types of wetting agents. The compositions can additionally contain solid pharmaceutical excipients such as starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, particularly for injectable solutions, include water, saline, aqueous dextrose, and glycols. For examples of carriers, stabilizers and adjuvants, see *Remington's Pharmaceutical Sciences*, edited by E. W. Martin (Mack Publishing Company, 18th ed., 1990). The compositions also can include stabilizers and preservatives.

As used herein, the term "therapeutically effective amount" is an amount sufficient to treat a specified disorder or disease or alternatively to obtain a pharmacological response treating a disorder or disease. Methods of determining the most effective means and dosage of administration can vary with the composition used for therapy, the purpose of the therapy, the target cell being treated, and the subject being treated. Treatment dosages generally may be titrated to optimize safety and efficacy. Single or multiple administrations can be carried out with the dose level and pattern being selected by the treating physician. Suitable dosage formulations and methods of administering the agents can be readily determined by those of skill in the art. For example, the composition are administered at about 0.01 mg/kg to about 200 mg/kg, about 0.1 mg/kg to about 100 mg/kg, or about 0.5 mg/kg to about 50 mg/kg. When the compounds described herein are co-administered with another agent or therapy, the effective amount may be less than when the agent is used alone.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer. If the composition is in the form of a gel, the composition may be rubbed onto a membrane of the patient, for example, the skin, preferably intact, clean, and dry skin, of the shoulder or upper arm and or the upper torso, and maintained thereon for a period of time sufficient for delivery of the present compound to the blood serum of the patient. The composition of the present invention in gel form may be contained in a tube, a sachet, or a metered pump. Such a tube or sachet may contain one unit dose, or more than one unit dose, of the composition. A metered pump may be capable of dispensing one metered dose of the composition.

This invention also provides the compositions as described above for intranasal administration. As such, the compositions can further comprise a permeation enhancer. Southall et al. *Developments in Nasal Drug Delivery*, 2000.

The present compound may be administered intranasally in a liquid form such as a solution, an emulsion, a suspension, drops, or in a solid form such as a powder, gel, or ointment.

Devices to deliver intranasal medications are well known in the art. Nasal drug delivery can be carried out using devices including, but not limited to, intranasal inhalers, intranasal spray devices, atomizers, nasal spray bottles, unit dose containers, pumps, droppers, squeeze bottles, nebulizers, metered dose inhalers (MDI), pressurized dose inhalers, insufflators, and bi-directional devices. The nasal delivery device can be metered to administer an accurate effective dosage amount to the nasal cavity. The nasal delivery device can be for single unit delivery or multiple unit delivery. In a specific example, the ViaNase Electronic Atomizer from Kurve Technology (Bethell, Wash.) can be used in this invention (http://www.kurvetech.com). The compounds of the present invention may also be delivered through a tube, a catheter, a syringe, a packtail, a pledget, a nasal tampon or by submucosal infusion. U.S. Patent Publication Nos. 20090326275, 20090291894, 20090281522 and 20090317377.

The present compound can be formulated as aerosols using standard procedures. The compound may be formulated with or without solvents, and formulated with or without carriers. The formulation may be a solution, or may be an aqueous emulsion with one or more surfactants. For example, an aerosol spray may be generated from pressurized container with a suitable propellant such as, dichlorodifluoromethane, trichlorofluoromethane, dichlorotetrafluoroethane, hydrocarbons, compressed air, nitrogen, carbon dioxide, or other suitable gas. The dosage unit can be determined by providing a valve to deliver a metered amount. Pump spray dispensers can dispense a metered dose or a dose having a specific particle or droplet size. As used herein, the term "aerosol" refers to a suspension of fine solid particles or liquid solution droplets in a gas. Specifically, aerosol includes a gas-borne suspension of droplets of a monoterpene (or sesquiterpene), as may be produced in any suitable device, such as an MDI, a nebulizer, or a mist sprayer. Aerosol also includes a dry powder composition of the composition of the instant invention suspended in air or other carrier gas. Gonda (1990) *Critical Reviews in Therapeutic Drug Carrier Systems* 6:273-313. Raeburn et al., (1992) *Pharmacol. Toxicol. Methods* 27:143-159.

The present compound may be delivered to the nasal cavity as a powder in a form such as microspheres delivered by a nasal insufflator. The present compound may be absorbed to a solid surface, for example, a carrier. The powder or microspheres may be administered in a dry, air-dispensable form. The powder or microspheres may be stored in a container of the insufflator. Alternatively the powder or microspheres may be filled into a capsule, such as a gelatin capsule, or other single dose unit adapted for nasal administration.

The pharmaceutical composition can be delivered to the nasal cavity by direct placement of the composition in the nasal cavity, for example, in the form of a gel, an ointment, a nasal emulsion, a lotion, a cream, a nasal tampon, a dropper, or a bioadhesive strip. In certain embodiments, it can be desirable to prolong the residence time of the pharmaceutical composition in the nasal cavity, for example, to enhance absorption. Thus, the pharmaceutical composition can optionally be formulated with a bioadhesive polymer, a gum (e.g., xanthan gum), chitosan (e.g., highly purified cationic polysaccharide), pectin (or any carbohydrate that thickens like a gel or emulsifies when applied to nasal mucosa), a microsphere (e.g., starch, albumin, dextran, cyclodextrin), gelatin, a liposome, carbamer, polyvinyl alcohol, alginate, acacia, chitosans and/or cellulose (e.g., methyl or propyl; hydroxyl or carboxy; carboxymethyl or hydroxylpropyl).

The composition containing the present compound can be administered by oral inhalation into the respiratory tract, i.e., the lungs.

Typical delivery systems for inhalable agents include nebulizer inhalers, dry powder inhalers (DPI), and metered-dose inhalers (MDI).

Nebulizer devices produce a stream of high velocity air that causes a therapeutic agent in the form of liquid to spray as a mist. The therapeutic agent is formulated in a liquid form such as a solution or a suspension of particles of suitable size. In one embodiment, the particles are micronized. The term "micronized" is defined as having about 90% or more of the particles with a diameter of less than about 10 μm. Suitable nebulizer devices are provided commercially, for example, by PARI GmbH (Starnberg, Germany). Other nebulizer devices include Respimat (Boehringer Ingelheim) and those disclosed in, for example, U.S. Pat. Nos. 7,568,480 and 6,123,068, and WO 97/12687. The present compound can be formulated for use in a nebulizer device as an aqueous solution or as a liquid suspension.

DPI devices typically administer a therapeutic agent in the form of a free flowing powder that can be dispersed in a patient's air-stream during inspiration. DPI devices which use an external energy source may also be used in the present invention. In order to achieve a free flowing powder, the present compound can be formulated with a suitable excipient (e.g., lactose). A dry powder formulation can be made, for example, by combining dry lactose having a particle size between about 1 μm and 100 μm with micronized particles of the present compound and dry blending. Alternatively, the compound can be formulated without excipients. The formulation is loaded into a dry powder dispenser, or into inhalation cartridges or capsules for use with a dry powder delivery device. Examples of DPI devices provided commercially include Diskhaler (GlaxoSmithKline, Research Triangle Park, N.C.) (see, e.g., U.S. Pat. No. 5,035,237); Diskus (GlaxoSmithKline) (see, e.g., U.S. Pat. No. 6,378,519; Turbuhaler (AstraZeneca, Wilmington, Del.) (see, e.g., U.S. Pat. No. 4,524,769); and Rotahaler (GlaxoSmithKline) (see, e.g., U.S. Pat. No. 4,353,365). Further examples of suitable DPI devices are described in U.S. Pat. Nos. 5,415,162, 5,239,993, and 5,715,810 and references therein.

MDI devices typically discharge a measured amount of the stored composition using compressed propellant gas. Formulations for MDI administration include a solution or suspension of an active ingredient in a liquefied propellant. Examples of propellants include hydrofluoroalklanes (HFA), such as 1,1,1,2-tetrafluoroethane (HFA 134a) and 1,1,1,2,3,3,3-heptafluoro-n-propane (HFA 227), and chlorofluorocarbons, such as $CCl_3F$. Additional components of HFA formulations for MDI administration include co-solvents, such as ethanol, pentane, water; and surfactants, such as sorbitan trioleate, oleic acid, lecithin, and glycerin. (See, for example, U.S. Pat. No. 5,225,183, EP 0717987, and WO 92/22286). The formulation is loaded into an aerosol canister, which forms a portion of an MDI device. Examples of MDI devices developed specifically for use with HFA propellants are provided in U.S. Pat. Nos. 6,006,745 and 6,143,227. For examples of processes of preparing suitable formulations and devices suitable for inhalation dosing see U.S. Pat. Nos. 6,268,533, 5,983,956, 5,874,063, and 6,221.398, and WO 99/53901, WO 00/61108, WO 99/55319 and WO 00/30614.

The present compound may be encapsulated in liposomes or microcapsules for delivery via inhalation. A liposome is a vesicle composed of a lipid bilayer membrane and an aqueous interior. The lipid membrane may be made of phospholipids, examples of which include phosphatidylcholine such as lecithin and lysolecithin; acidic phospholipids such as phosphatidylserine and phosphatidylglycerol; and sphingophospholipids such as phosphatidylethanolamine and sphingomyelin. Alternatively, cholesterol may be added. A microcapsule is a particle coated with a coating material. For example, the coating material may consist of a mixture of a film-forming polymer, a hydrophobic plasticizer, a surface activating agent or/and a lubricant nitrogen-containing polymer. U.S. Pat. Nos. 6,313,176 and 7,563,768.

The present compound may also be used alone or in combination with other chemotherapeutic agents via topical application for the treatment of localized cancers such as breast cancer or melanomas. The present compound may also be used in combination with narcotics or analgesics for transdermal delivery of pain medication.

This invention also provides the compositions as described above for ocular administration. As such, the compositions can further comprise a permeation enhancer. For ocular administration, the compositions described herein can be formulated as a solution, emulsion, suspension, etc. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851.

The present compound can be given alone or in combination with other drugs for the treatment of the above diseases for a short or prolonged period of time. The present compositions can be administered to a mammal, preferably a human. Mammals include, but are not limited to, murines, rats, rabbit, simians, bovines, ovine, porcine, canines, feline, farm animals, sport animals, pets, equine, and primates.

The invention also provides a method for inhibiting the growth of a cell in vitro, ex vivo or in vivo, where a cell, such as a cancer cell, is contacted with an effective amount of the present compound as described herein.

Pathological cells or tissue such as hyperproliferative cells or tissue may be treated by contacting the cells or tissue with an effective amount of a composition of this invention. The cells, such as cancer cells, can be primary cancer cells or can be cultured cells available from tissue banks such as the American Type Culture Collection (ATCC). The pathological cells can be cells of a systemic cancer, gliomas, meningiomas, pituitary adenomas, or a CNS metastasis from a systemic cancer, lung cancer, prostate cancer, breast cancer, hematopoietic cancer or ovarian cancer. The cells can be from a vertebrate, preferably a mammal, more preferably a human. U.S. Patent Publication No. 2004/0087651. Balassiano et al. (2002) *Intern. J. Mol. Med.* 10:785-788. Thorne, et al. (2004) *Neuroscience* 127:481-496. Fernandes, at al. (2005) *Oncology Reports* 13:943-947. Da Fonseca, et al. (2008) *Surgical Neurology* 70:259267. Da Fonseca, et al. (2008) *Arch. Immunol. Ther. Exp.* 56:267-276. Hashizume, et al. (2008) *Neuroncology* 10:112-120.

In vitro efficacy of the present composition can be determined using methods well known in the art. For example, the cytoxicity of the present compound may be studied by MTT [3-(4,5-dimethylthiazol-2-yl)-2,5-diphenyl tetrazolium bromide]cytotoxicity assay. MIT assay is based on the principle of uptake of MTT, a tetrazolium salt, by metabolically active cells where it is metabolized into a blue colored formazon product, which can be read spectrometrically. *J. of*

*Immunological Methods* 65: 55 63, 1983. The cytoxicity of the present compound may be studied by colony formation assay. Functional assays for inhibition of VEGF secretion and IL-8 secretion may be performed via ELISA. Cell cycle block by the present compound may be studied by standard propidium iodine (PI) staining and flow cytometry. Invasion inhibition may be studied by Boyden chambers. In this assay a layer of reconstituted basement membrane. Matrigel, is coated onto chemotaxis filters and acts as a barrier to the migration of cells in the Boyden chambers. Only cells with invasive capacity can cross the Matrigel barrier. Other assays include, but are not limited to, cell viability assays, apoptosis assays, and morphological assays.

The following are examples of the present invention and are not to be construed as limiting.

EXAMPLES

Example 1: Synthesis of Iso-POH

The reaction scheme is the following:

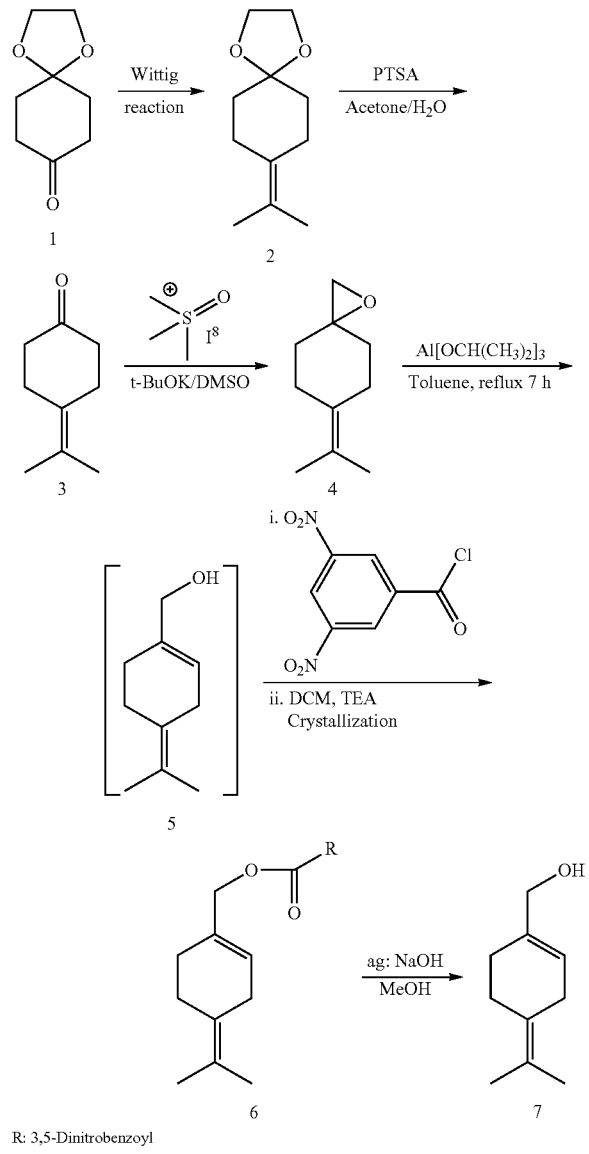

R: 3,5-Dinitrobenzoyl

Preparation of 4-isopropylidene-1,4-dioxa-spiro[4.5] decane (2)

Isopropyltriphenylphosphonium iodide (83.02 g, 192 mmol) was added to NaH (60%, in mineral oil, 8.38 g, 192 mmol) in dry dimethyl sulfoxide (120 mL) at room temperature under a nitrogen atmosphere. The reaction mixture was slowly heated to 50° C. over a period of 15 min and maintained at 50° C. until the reaction mass became a red color (approximately 30 min). A solution of 1,4-cyclohexanedione monoethylene ketal (1, 30 g, 192 mmol) in dry dimethyl sulfoxide was added over a period of 45 min while keeping the temperature below 50° C. and the reaction was maintained at 50° C. for 16 h. The reaction mixture was cooled to room temperature, quenched with cold water (150 ml), and extracted with ethyl acetate (2×160 mL). The combined organic layer was washed with water (2×200 mL), followed by brine (10%, 250 mL) and dried over sodium sulfate. The filtered organic layer was concentrated to give a solid which was triturated with hexanes (300 mL) and the precipitated triphenylphosphine oxide was filtered off. The hexane layer was concentrated to give an oil which was purified by column chromatography. [Column dimensions: dia: 6.0 cm, height: 12 cm, silica: 200 mesh, eluted hexanes (1.0 L) followed by hexane:ethyl acetate (97:3, 2.0 L)] The hexane:ethyl acetate fractions were combined and concentrated under vacuum to give an oil. Weight: 23.36 g. Weight yield: 66.7%. $^1$H-NMR (400 MHz, CDCl$_3$): δ 1.61-1.63 (t, 4H), 1.64 (s, 6H), 2.29 (m, 4H), 3.97 (s, 4H). MS (APCI method): No molecular ion peak was observed.

Preparation of 4-isopropylidene cyclohexanone (3)

p-Toluenesulfonic acid (31.16 g, 164 mmol) was added to a solution of ketal (2, 23.0 g, 126 mmol) in acetone (2.3 L) and water (138 mL). The reaction mixture was heated to reflux and maintained at reflux for 3.5 h. The mixture was cooled to room temperature, treated with saturated sodium bicarbonate (60 mL) and concentrated under vacuum. The resulting oily residue was extracted with ethyl acetate (2×130 mL), washed with water (100 mL), then brine (100 mL), and dried over sodium sulfate. The filtered organic layer was concentrated under vacuum to give an oil. Weight: 16 g. Weight yield: 92%. $^1$H-NMR (400 MHz, CDCl$_3$): δ 1.69 (s, 61H), 2.35 (t, 4H), 2.50 (t, 4H). MS (APCI method): No molecular ion peak was observed (Note: $^1$H-NMR showed the presence of ~2% of ketal 2 but used without purification).

Preparation of 4-isopropylidene-1-oxa-spiro[2.5]octane (4)

Potassium t-butoxide (3.3 g, 29.4 mmol) was added to a mixture of ketone (3, 2.5 g, 18.1 mmol) and trimethylsulfoxonium iodide (6.45 g, 29.4 mmol) in dry dimethyl sulfoxide (40 mL) under nitrogen atmosphere at room temperature. The mixture was stirred for 4.0 h at room temperature. The reaction was quenched by the addition of cold water (40 mL) and extracted with ethyl acetate (2×60 mL). The combined organic layer was washed with water (75 mL) followed by brine (75 mL) and dried over sodium sulfate. The filtered organic layer was concentrated under vacuum to give an oil. Weight: 2.13 g. Weight yield: 77%. $^1$H-NMR (400 MHz, CDCl$_3$): δ 1.42-1.50 (m, 2H), 1.55-1.61 (m, 2H), 1.65 (s, 6H), 2.31 (t, 4H), 2.61 (s, 2H). MS (APCI method): No molecular ion peak was observed.

Preparation of 3,5-dinitrobenzoic acid 4-isopropylidene cyclohex-1-enylmethyl ester (6)

Aluminum isopropoxide (5.93 g, 29.0 mmol) was added to a mixture of epoxide (4, 4.0 g, 26.2 mmol) in toluene (80 mL) and the mixture was heated to reflux for 7.0 h. The mixture was cooled to room temperature and quenched with saturated potassium sodium tartrate solution. The organic layer was separated, washed with water (40 mL), followed by brine (40 mL), and dried over sodium sulfate. The filtered organic layer was concentrated under vacuum to give crude isoperillyl alcohol (5) as an oil. Weight: 4.0 g, Weight yield: 100%, Purity: ~85-90% (by GC area percent, Actual yield ca; 85%).

Triethylamine (5.1 mL, 36.6 mmol) was added to a solution of crude isoperillyl alcohol (5, 4.0 g, 26.2 mmol) in dichloromethane (50 mL). After stirring for 15 min, 3,5-dinitrobenzoyl chloride (6.3 g, 27.5 mmol) was added over a period of 0.25 h. The reaction mixture was stirred for 3.0 h and quenched with water (30 mL). The organic layer was separated, washed with water (40 mL), and dried over sodium sulfate. The filtered organic layer was concentrated under vacuum to give a pale yellow solid (8.5 g), which was recrystallized from acetone to give pure ester 6 as a pale yellow solid. Mp: 138-140° C. (acetone). Weight: 5.7 g, Yield: 62% (from epoxide). $^1$H-NMR (400 MHz, CDCl$_3$): δ 1.68 (s, 3H), 1.71 (s, 3H), 2.18 (t, 2H), 2.40 (t, 21H), 2.87 (br s, 2H), 4.85 (s, 2H); 5.88 (s, 1H), 9.17 (t, 1H), 9.24 (s, 1H). MS (APCI method): m/e: 247.1 (5%), 149.07 (7%), 135.1 (100%), 107.1 (9%).

Preparation of isoperillyl alcohol (7)

Aqueous sodium hydroxide (1.43 g, 35.7 mmol, dissolved in 12.5 mL of water) was added to an ice cold solution of 3,5-dinitrobenzoic acid 4-isopropylidene-cyclohex-1-enyl-methyl ester (6, 5.63 g, 16.2 mmol) in methanol (56 mL) over a period of 0.25 h. The reaction mixture was allowed to warm to room temperature and then stirred for 3.0 h. The methanol was concentrated under vacuum to a minimum stirring volume and the mixture was suspended in water (40 mL). The resulting mixture was extracted with ethyl acetate (2×50 mL). The organic layer was washed with water (2×50 mL), then brine (50 mL), and dried over sodium sulfate. The filtered organic layer was concentrated under vacuum to give pure isoperillyl alcohol as an oil. Weight: 2.35 g. Yield: 95%, Purity: 97% (by GC AUC). $^1$H-NMR (400 MHz, CDCl$_3$): δ 1.65 (s, 3H), 1.69 (s, 3H), 1.77 (bs, OH), 2.09 (m, 2H), 2.33 (t, 2H), 2.79 (br s, 2H); $^{13}$C-NMR: δ 20.38, 20.80, 26.95, 27.60, 29.86, 67.49, 122.88, 123.04, 127.92, 138.37. MS (APCI method): m/e: 152 (M$^+$, 3.5%), 135.07 (100%), 107.12 (5%). However, the mass spectrum showed four small peaks (~5%) at M+: 207.06, 269.1, 287.09 & 301 which were not characterized.

Example 2: Alternative Synthesis of Iso-POH

The reaction scheme is the following:

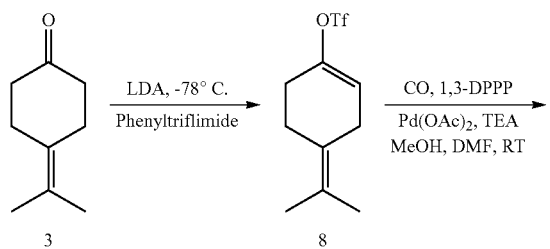

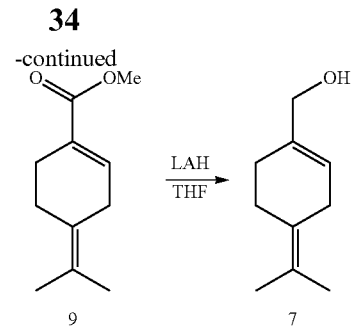

Preparation of trifluoromethanesulfonic acid 4-isopropylidenecyclohex-1-enyl ester (8)

2.5 M solution of n-Butyl lithium in hexanes (5.6 mL, 14.1 mmol) was added to a solution of diisopropylamine (1.98 mL, 14.1 mmol) in dry THF (30 mL) at −78° C. over a period of 0.5 hr. After stirring for 1.0 h at −78° C., a solution of ketone (3, 1.3 g, 9.4 mmol) in dry THF (10 mL) was added over a period of 10 min while maintaining the temperature below −78° C. The reaction mixture was stirred for 1.0 h at −78° C. A solution of phenyltriflimide (3.53 g, 9.86 mmol) in THF (15 mL) was added slowly while maintaining the temperature below −78° C. The reaction mixture was slowly warmed to 0° C. maintained for 2.0 h at 0° C. and then quenched with satd ammonium chloride solution. The separated organic layer was washed with water (15 mL), brine (15 mL) and dried over sodium sulfate. The filtered organic layer was concentrated under vacuum and the resulting residue was purified by column chromatography. [Column dimensions: dia: 6.0 cm, height: 12 cm, silica: 200 mesh, eluted with hexanes (200 mL)] The similar fractions were combined and concentrated under vacuum which gave an oil. Weight: 0.9 g. Weight yield: 38%. $^1$H-NMR (400 MHz, CDCl$_3$): δ 1.68 (s, 3H), 1.71 (s, 3H), 2.37 (m, 2H), 2.46 (m, 2H), 2.91 (m, 2H), 5.73 (m, 1H). MS (APCI method): No molecular ion peak was observed.

Note-1: $^1$H-NMR indicated the presence of aromatic peaks (~5%) between δ 7.42-7.57 which were attributed to the by-product trifluoro-N-phenylmethanesulfonamide.

Note-2: The compound 8 was also synthesized in low yield (28%) using triflic anhydride in the presence of 2,6-di-tert-butyl-4-methylpyridine as a base.

Preparation of 4-isopropylidene cyclohex-1-enecarboxylic acid methyl ester (9)

To a solution of compound 8 (0.2 g, 0.74 mmol) in N'N-dimethylformamide (1.5 mL) was added methanol (1.0 mL), triethylamine (0.17 mL, 1.2 mmol), 1,3-bis(diphenyl-phosphino)propane (0.03 g, 0.07 mmol) and palladium acetate (0.04 g, 0.07 mmol). The reaction mixture was degassed and then stirred at room temperature under carbon monoxide (balloon pressure) for 5 h. The reaction mixture was diluted with ethyl acetate (15 mL) and washed with 0.5 N HCl (15 mL), brine (15 mL) and dried over sodium sulfate. The filtered organic layer was concentrated under vacuum and the resulting residue was purified by column chromatography. [Column dimensions: dia: 6.0 cm, height: 12 cm, silica: 200 mesh, eluted with hexanes (100 mL) followed by ethyl acetate:hexanes (2%, 150 mL)] The similar fractions were combined and concentrated under vacuum which gave an oil. While TLC analysis showed only a single spot, $^1$H-NMR and GC analysis indicated that the isolated material was a mixture of two primary components that co-eluted by TLC. Weight: 0.11 g. Weight yield: 82%. $^1$H-NMR (400 MHz, CDCl$_3$) indicated the presence of peaks corresponding to the methyl ester (9) along with an unknown impurity. GC analysis confirmed that it is mainly a mixture of two compounds with a ratio of 3:1. MS (APCI method): m/e: 180 (M$^+$, 5%), 180.9 (M$^{+1}$, 100%). The other peaks (≤5%) at M+: 197.8, 247.0 & 274.0 were not characterized. The crude mixture was taken forward without purification.

Preparation of isoperillyl alcohol (7)

Methyl ester (9, 0.11 g, 0.6 mmol) in dry THF (10 mL) was added to a cold solution of LAH (0.03 g, 0.78 mmol) in dry THF (10 mL) over a period of 2 min. The reaction mixture was slowly heated to reflux and maintained for 3.0 h. The mixture was cooled to 5° C. and quenched with satd sodium sulfate (1.5 mL). The precipitated lithium salts were filtered off and washed with hot ethyl acetate (20 mL). The filtrate was dried over sodium sulfate. The filtered organic layer was concentrated under vacuum which gave an oil. Weight: 74 mg. Weight yield: 79%. While TLC analysis showed only a single spot, $^1$H-NMR and GC analysis indicated that the isolated material was a mixture of two primary components that co-eluted by TLC. $^1$H-NMR (400 MHz, CDCl$_3$) indicated the presence of peaks corresponding to the isoperillyl alcohol (7) along with an unknown impurity. MS (APCI method): m/e: 153 (M$^{+1}$, 40%), 152 (M$^+$, 13%), 135.09 (M-OH). The other peaks at M+: 169.03 (10%), 255.20, (13%), 285.25 (15%), 287.19 (70%), 290 (68%), & 397.24 (15%) were not characterized. GC analysis confirmed the presence of isoperillyl alcohol (20.5%, (AUC)), compared with the iso-POH obtained from the epoxide route along with the unknown impurity (67.5%, (AUC)).

Figure 1:
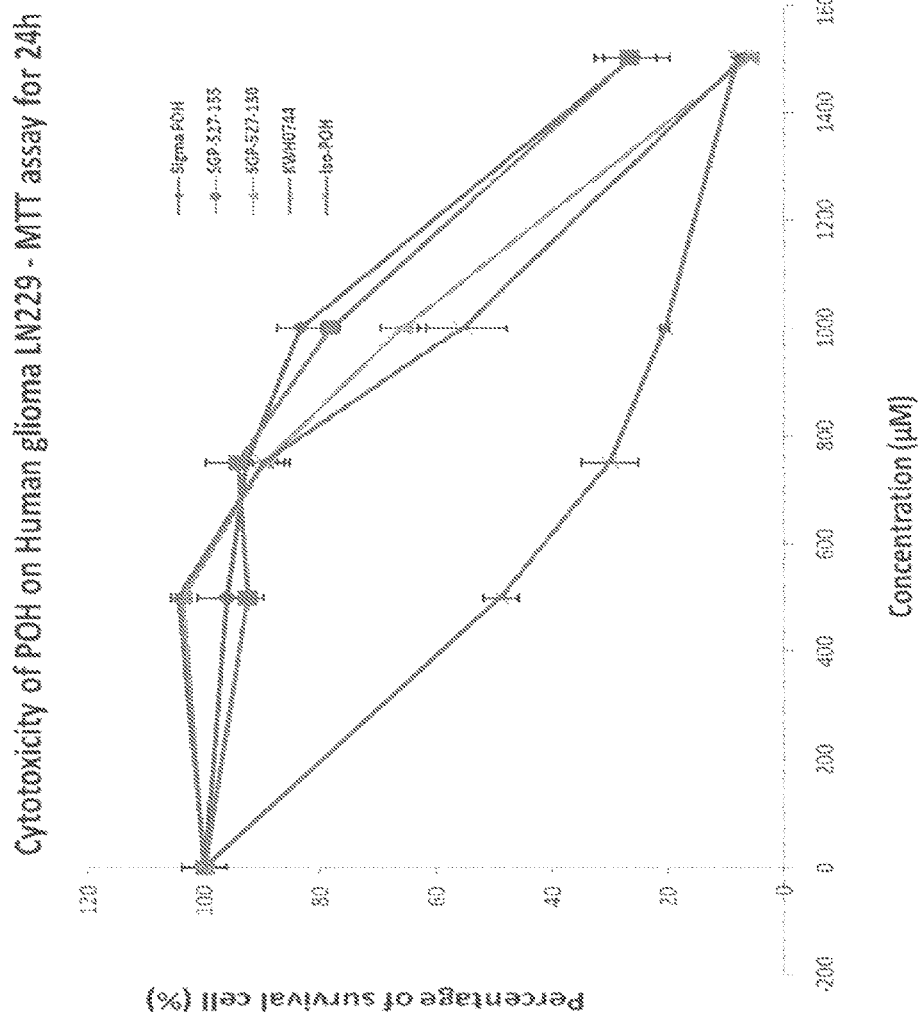
FIG. 1 shows the results of the MTT cytotoxicity assays demonstrating the efficacy of different types of POH and iso-POH in killing LN229 human glioma cells.
Figure 2:
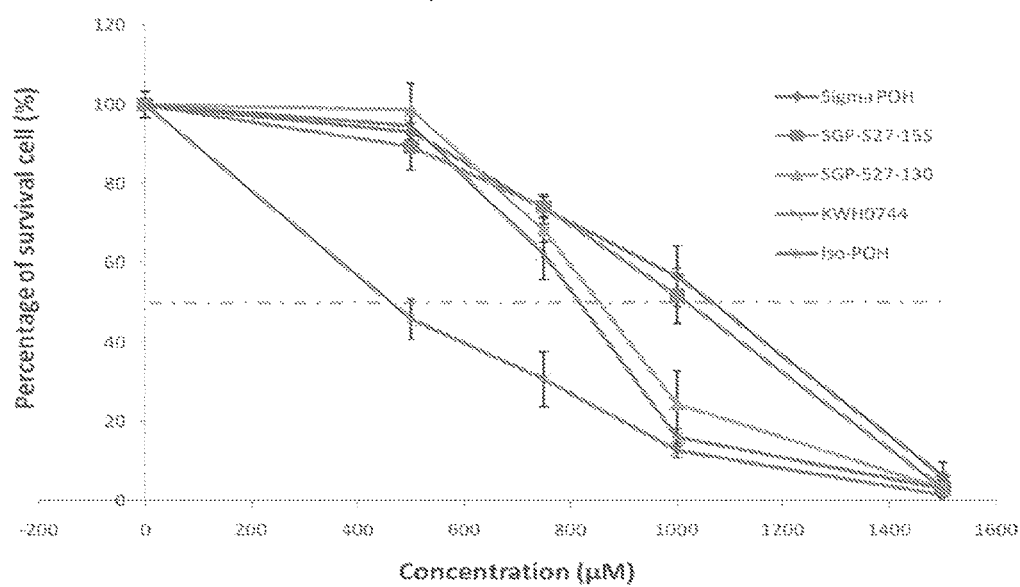
FIG. 2 shows the results of the MTT cytotoxicity assays demonstrating the efficacy of different types of POH and iso-POH in killing U251 human glioma cells.
Figure 3:
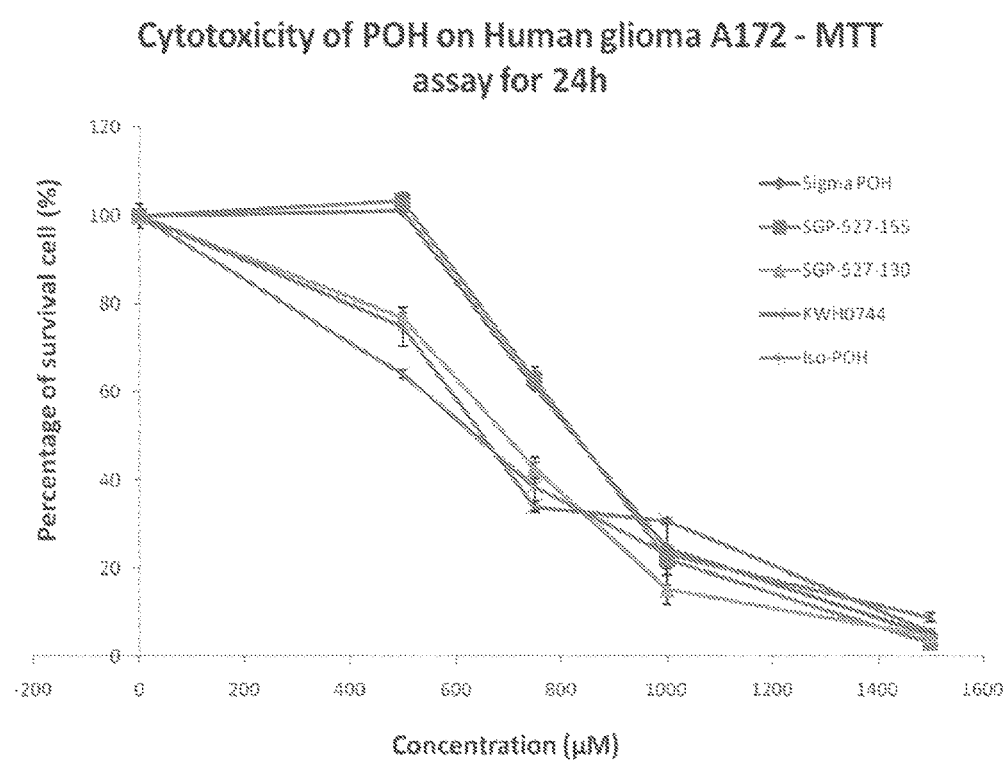
FIG. 3 shows the results of the MTT cytotoxicity assays demonstrating the efficacy of different types of POH and iso-POH in killing A172 human glioma cells.

Example 3: In vitro Cytotoxicity Studies of Iso-POH ((4-Isopropylidene cyclohex-1-enyl)-methanol The MTT cytotoxicity assays were carried out after cells were treated with iso-POH (e.g., synthesized by the method in Example 1) or other types of POH with different purity. FIG. 1 shows the results of the MTT cytotoxicity assays demonstrating the efficacy of different types of POH and iso-POH in killing LN229 human glioma cells. Sigma POH is the POH purchased from Sigma Chemicals having a purity of about 96%. SGP-527-155 was prepared from the WAKO POH by two-fold crystallization from di-isopropyl ether solvent, and has a GC relative area purity of about 98.7% (area under the curve). KWH0744 is the crude POH purchased from Wako having a purity of about 89.5%. SGP-527-130 was prepared from the WAKO POH by single crystallization from di-isopropyl ether solvent, and has a GC relative area purity of about 97.1% (area under the curve). FIG. 2 shows the results of the MTT cytotoxicity assays demonstrating the efficacy of different types of POH and iso-POH in killing U1251 human glioma cells. FIG. 3 shows the results of the MTT cytotoxicity assays demonstrating the efficacy of different types of POH and iso-POH in killing A172 human glioma cells. The results suggest that iso-POH exhibited much better cytotoxicity than POH with different purity.

Figure 4A:
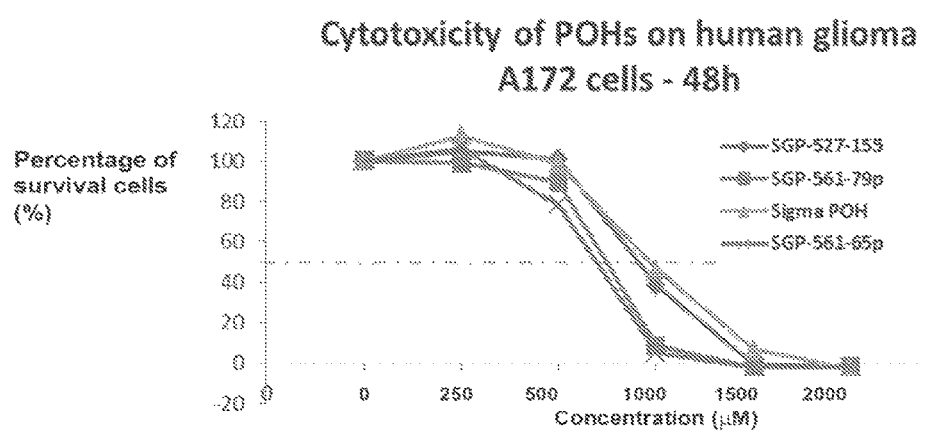
FIGS. 4A and 4B show the results of the MTT cytotoxicity assays demonstrating the efficacy of different types of POH and iso-POH in killing A172 human glioma cells (temozolomide-sensitive) (FIG. 4A) and A172 temozolomide-resistant cells (FIG. 4B). SGP-527-155 is the POH purified to the GLP quality (with a GC relative area purity (area under the curve) of about 98.7%). SGP-561-79P and SGP-561-65P are two different batches of Iso-POH. SGP-561-79P is more purified than SGP-561-65P and the details are as follows.
Figure 4B:
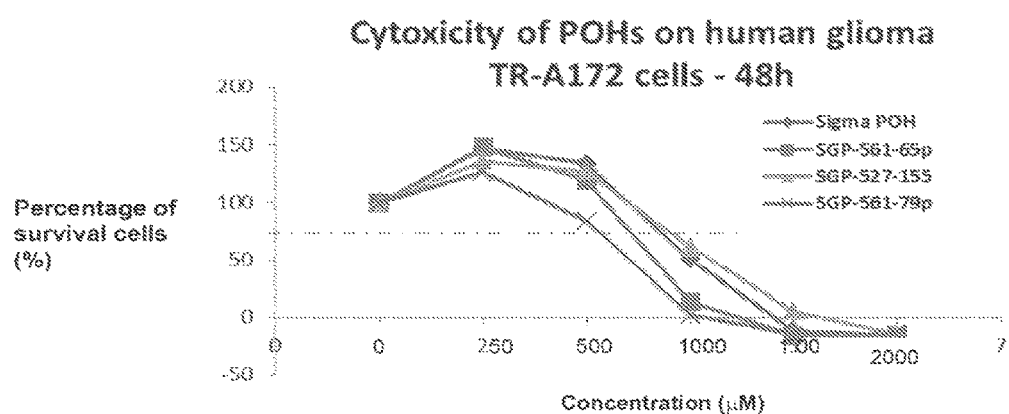

In vitro cytotoxicity of iso-POH in temozolomide-sensitive or temozolomide-resistant cells were also studied. Glioma cells were treated with Sigma POH, POH synthesized to GLP quality (SGP-527-155) having a purity of about 98.7%, and iso-POH (SGP-561-79P, SGP-561-65P) for 48 hours and MTT assay performed. FIG. 4 demonstrates that A172 cells had the greatest cytotoxic response to iso-POH compared to GLP POH and Sigma POH (FIG. 4A). This response pattern was also seen in A172 temozolomide resistant cells (FIG. 4B). Similarly. FIG. 5 demonstrates that U251 cells had the greatest response to iso-POH (FIG. 5A), and that this response was also seen in U251 temozolomide resistant cells (FIG. 5B). The same response to iso-POH was seen in LN229 temozolomide sensitive (FIG. 6A) and temozolomide resistant cells (FIG. 6B). U87 cells, both temozolomide sensitive (FIG. 7A) and resistant (FIG. 7B), had the greatest response to iso-POH, albeit less than LN229 and U251 cells.

FIG. 8 shows the results of the MTT assays performed using TMZ sensitive U251 glioma cells over 24 hours using Sigma POH, GLP POH having a purity of about 98.7%, iso-POH (Iso-POH65, Iso-POH79) all at 0 mM-3 mM concentration. Iso-POH had greater cytotoxicity compared to Sigma POH and GLP POH (FIG. 8A). U251 temozolomide resistant cell line (U251-TR2) treated under same conditions demonstrated greater cytotoxicity with iso-POH compared to Sigma and GLP POH (FIG. 8B). Another U251 temozolomide resistant cell line (U251-TR1) treated under same conditions also demonstrated greater cytotoxicity with iso-POH (iso-POH65, iso-POH79) compared to GLP POH or Sigma POH (FIG. 8C).

FIG. 9 shows the results of the MTT assay performed using glioblastoma cancer stem cell line USC04 treated with both GLP-POH and iso-POH (Iso-POH65) over 24 hrs. GLP POH and iso-POH demonstrated similar cytoxicity on the cells.

U251 TMZ-sensitive and TMZ-resistant (U251-TR1, U251-TR2) cells were treated with Sigma POH (1.5 mM) or GLP POH (1.5 mM) for 18 hours, then Western blot was performed. The results show that Sigma POH and GLP POH increased expression of glucose-regulatory protein 78 (GRP-78) and the apoptosis marker CHOP, suggesting increased endoplasmic reticulum (ER) stress after treatment (FIG. 10a). Under the same conditions, iso-POH (iso-POH65, iso-POH79) also increased ER stress (FIG. 10b).

U251 glioma cells were treated with 500 µM Sigma POH, GLP POH or iso-POH (isoPOH65, isoPOH79) for 24 hours, then Western blot was performed. The results (FIG. 11) demonstrate that all treatments decreased Kras expression.

Example 4: Synthesis of Iso-POH Conjugated with Temozolamide (TMZ)

The reaction scheme is the following:

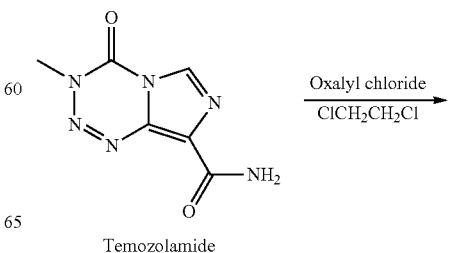

Temozolamide

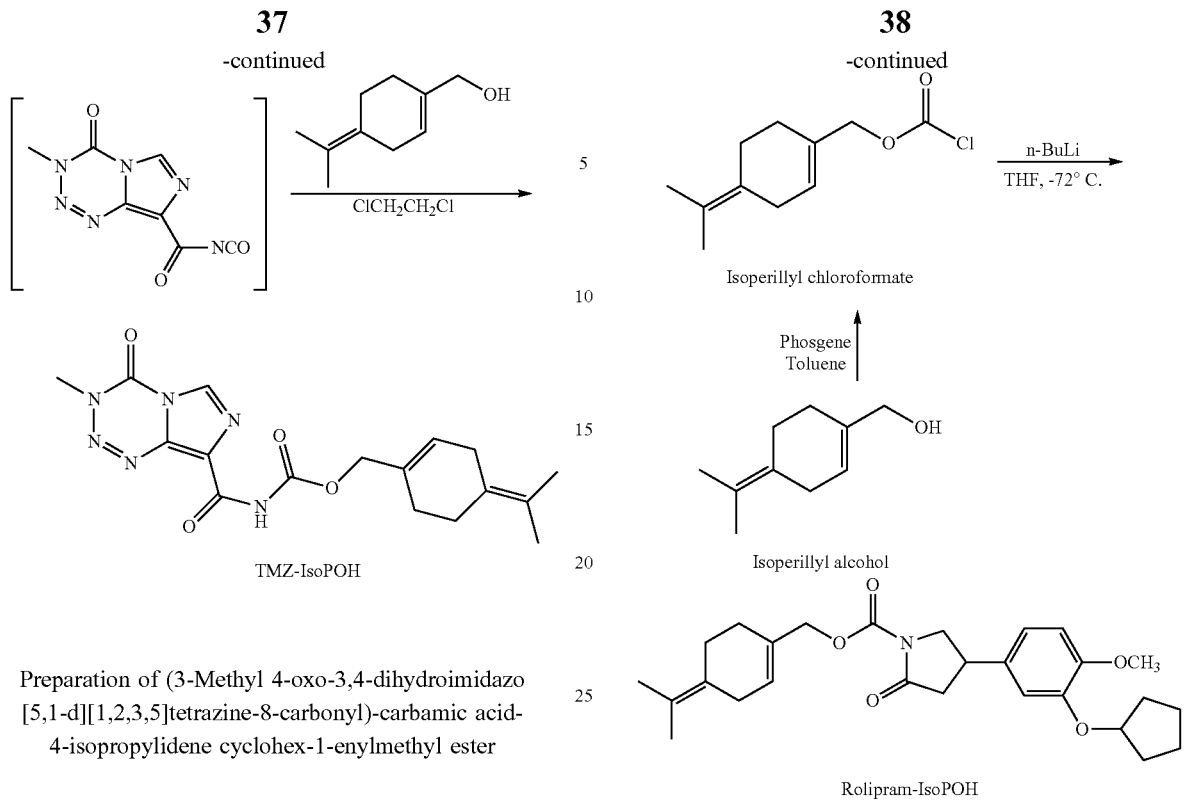

Preparation of (3-Methyl 4-oxo-3,4-dihydroimidazo [5,1-d][1,2,3,5]tetrazine-8-carbonyl)-carbamic acid-4-isopropylidene cyclohex-1-enylmethyl ester Oxalyl chloride (0.26 g, 2.0 mmol) will be added slowly to a mixture of Temozolamide (Source: OChem Incorporation, Lot #0711185A; 0.2 g, 1.0 mmol) in 1,2-dichloroethane (15 mL) over a period of 5 min while maintaining the temperature at 10° C. under $N_2$. The reaction mixture will be allowed to warm to room temperature and then heated to reflux for 2.5 h. The excess of oxalyl chloride and 1,2-dichloroethane will be removed by concentration under vacuum. The resulting residue will be redissolved in 1,2-dichloroethane (20 mL) and the reaction mixture cooled to 5° C. under $N_2$. A solution of isoperillyl alcohol (0.17 g, 1.12 mmol) in 1,2-dichloroethane (5 mL) will be added over a period of 10 min. The reaction mixture will be allowed to warm to room temperature and stirred for 12 h. 1,2-Dichloroethane will be concentrated under vacuum to give a residue which will be triturated with hexanes. The resulting pale yellow solid will be filtered and washed with hexanes.

Example 5: Synthesis of Iso-POH Conjugated with Rolipram

The reaction scheme is as follows.

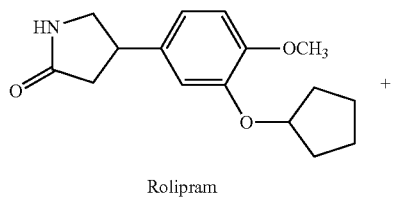

Rolipram

Preparation of 4-(3-Cyclopentyloxy-4-methoxyphenyl)-2-oxo-pyrrolidine-1-carboxylic acid 4-isopropylidene cyclohex-1-enylmethyl ester Phosgene (20% in toluene, 19.5 ml, 39.4 mmol) will be added to a mixture of isoperillyl alcohol (3.0 g, 19.7 mmol) and potassium carbonate (8.1 g, 58.6 mmol) in dry toluene (45 mL) over a period of 45 min while maintaining the temperature between 10-12° C. The reaction mixture will be allowed to warm to room temperature and stirred for 10 h under $N_2$. The reaction mixture will be quenched with water (40 mL) and the organic layer separated. The aqueous layer will be extracted with toluene (30 mL) and the combined organic layer washed with water (40 mL×2), brine (10%, 40 mL), and dried over sodium sulfate (25 g). The filtered organic layer will be concentrated under vacuum to give isoperillyl chloroformate as an oil.

Butyl lithium (2.5 M, 0.36 mL, 0.90 mmol) will be added to a solution of rolipram (Source: GL synthesis, Inc. Lot #GLS-SH-110809; 0.2 g, 0.72 mmol) in dry THF (8 mL) at −72° C. over a period of 10 min under $N_2$. After the reaction mixture being stirred for 1.0 h at −72° C., isoperillyl chloroformate (0.16 g, 0.76 mmol, dissolved in 4 mL THF) will be added over a period of 10 min while maintaining the temperature at −72° C. The reaction mixture will be stirred for 3 h and quenched with saturated ammonium chloride (10 mL). The reaction mixture will be allowed to warm to room temperature and extracted with ethyl acetate (2×20 mL). The combined organic layer will be washed with water (20 mL), brine (10%, 25 mL), and dried over sodium sulfate. The filtered organic layer will be concentrated to give an oil which will be purified by column chromatography [Column dimensions: dia: 1.5 cm, height: 15 cm, silica: 230-400 mesh] and eluted with a mixture of 5% ethyl acetate/hexanes (120 mL) followed by 10% ethyl acetate/hexanes (150 mL).

The 10% ethyl acetate/hexanes fractions will be combined and concentrated under vacuum to give a gummy solid.

Example 6: Synthesis of Dimethyl Celecoxib bis iso-POH carbamate conjugate

The reaction scheme is as follows.

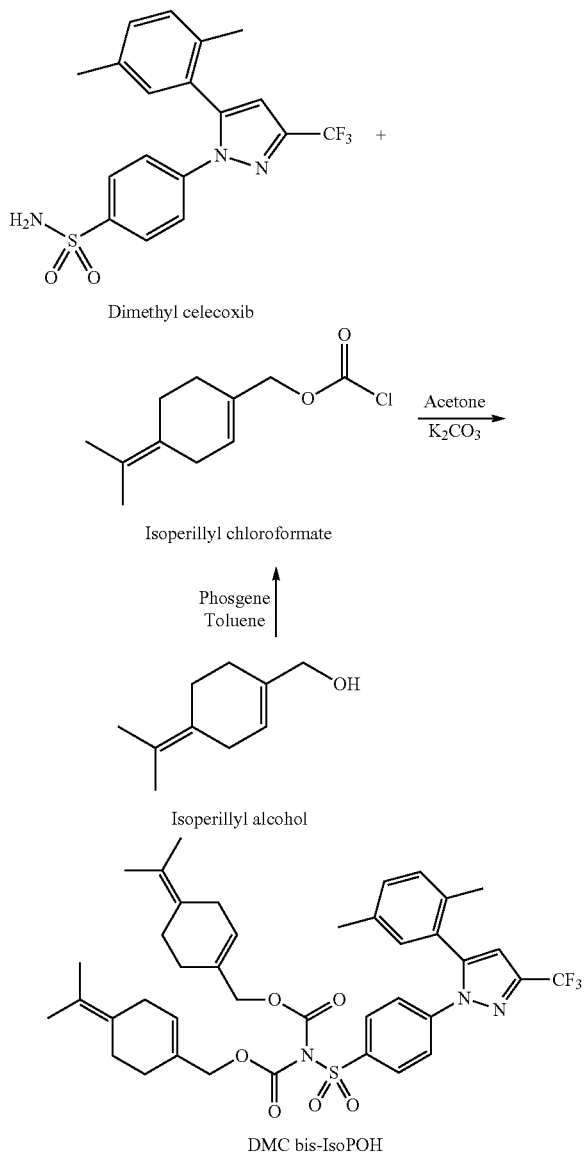

Preparation of 4-(Bis-N,N'-4-isopropylidene cyclohex-1-enylmethyloxy carbonyl[5-(2,5-dimethyl phenyl)-3-trifluoromethyl pyrazol-1-yl]benzenesulfonamide Phosgene (20% in toluene, 19.5 ml, 39.4 mmol) will be added to a mixture of isoperillyl alcohol (3.0 g, 19.7 mmol) and potassium carbonate (8.1 g, 58.6 mmol) in dry toluene (45 mL) over a period of 45 min while maintaining the temperature between 10-12° C. The reaction mixture will be allowed to warm to room temperature and stirred for 10 h under $N_2$. The reaction mixture will be quenched with water (40 mL) and the organic layer separated. The aqueous layer will be extracted with toluene (30 mL) and the combined organic layer washed with water (40 mL×2), brine (10%, 40 mL), and dried over sodium sulfate (25 g). The filtered organic layer will be concentrated under vacuum to give isoperillyl chloroformate as an oil.

Isoperillyl chloroformate (0.22 g, 1.0 mmol) will be added slowly to a mixture of dimethyl celecoxib (0.2 g, 0.50 mmol) and potassium carbonate (0.14 g, 1.0 mmol) in dry acetone (25 mL) over a period of 5 min under $N_2$. The reaction mixture will be heated to reflux and maintained for 4 h. The reaction mixture will be cooled and the acetone concentrated under vacuum. The resulting residue will be suspended in water (25 mL) and extracted with ethyl acetate (3×20 mL). The combined organic layer will be washed with water (40 mL), followed by brine (10%, 30 mL), and dried over sodium sulfate. The filtered organic layer will be concentrated under vacuum to give a residue which will be purified by column chromatography [Column dimensions: dia: 1.5 cm, height: 15 cm, silica: 230-400 mesh] and eluted with hexanes (100 mL) followed by a mixture of hexanes/ethyl acetate (95:5, 100 mL). The hexane/ethyl acetate fractions will be combined and concentrated under vacuum to give a gummy mass.

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

What is claimed is:

1. A pharmaceutical composition comprising an isoperillyl alcohol carbamate, wherein the isoperillyl alcohol carbamate is an isoperrilyl alcohol covalently bound via a carbamate linking group to temozolomide (TMZ).

2. The pharmaceutical composition of claim 1, wherein the pharmaceutical composition is administered by inhalation, intranasally, orally, intravenously, subcutaneously or intramuscularly.

3. The pharmaceutical composition of claim 1, wherein the pharmaceutical composition is admixed or coformulated with a therapeutic agent.

4. The pharmaceutical composition of claim 1, wherein the isoperillyl alcohol is selected from the group consisting of (4-isopropylidene cyclohex-1-enyl)methanol, (4-isopropyl cyclohexa-1,3-dienyl)methanol, (4-isopropyl cyclohexa-1,4-dienyl)methanol, (4-isopropylphenyl)methanol and (4-isopropenylphenyl)methanol.

5. The pharmaceutical composition of claim 1, wherein the isoperillyl alcohol is 4-isopropylidene cyclohex-1-enyl)methanol.

6. A method for treating glioblastoma in a mammal, comprising the step of administering to the mammal the pharmaceutical composition of claim 1.

7. The method of claim 6, further comprising the step of treating the mammal with radiation.

8. The method of claim 6, further comprising the step of administering to the mammal a chemotherapeutic agent.

9. The method of claim 6, wherein the pharmaceutical composition is administered by inhalation, intranasally, orally, intravenously, subcutaneously or intramuscularly.

\* \* \* \* \*

UNITED STATES PATENT AND TRADEMARK OFFICE
CERTIFICATE OF CORRECTION

PATENT NO. : 9,987,237 B2
APPLICATION NO. : 14/833210
DATED : June 5, 2018
INVENTOR(S) : Chen et al.

It is certified that error appears in the above-identified patent and that said Letters Patent is hereby corrected as shown below:

On the Title Page

(72) Inventors:
Change "Pupalli" to --Puppali--

Signed and Sealed this
Ninth Day of May, 2023

Katherine Kelly Vidal
*Director of the United States Patent and Trademark Office*